US010101322B2

(12) United States Patent
Natarajan et al.

(10) Patent No.: US 10,101,322 B2
(45) Date of Patent: Oct. 16, 2018

(54) PHOTOACTIVATED CHEMICAL BLEACHING OF DYES USING BORATES

(71) Applicant: GENERAL ELECTRIC COMPANY, Schenectady, NY (US)

(72) Inventors: Arunkumar Natarajan, Niskayuna, NY (US); Anup Sood, Clifton Park, NY (US); Lakshmi Sireesha Kaanumalle, Niskayuna, NY (US); Christina Lowes, Clifton Park, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 730 days.

(21) Appl. No.: 14/621,715

(22) Filed: Feb. 13, 2015

(65) Prior Publication Data
US 2016/0238592 A1 Aug. 18, 2016

(51) Int. Cl.
G01N 33/536 (2006.01)
G01N 33/58 (2006.01)
G01N 21/64 (2006.01)
G01N 1/30 (2006.01)

(52) U.S. Cl.
CPC ....... *G01N 33/536* (2013.01); *G01N 21/6428* (2013.01); *G01N 33/582* (2013.01); *G01N 1/30* (2013.01); *G01N 2001/302* (2013.01)

(58) Field of Classification Search
None
See application file for complete search history.

(56) References Cited

U.S. PATENT DOCUMENTS

| | | | |
|---|---|---|---|
| 4,307,182 A | 12/1981 | Dalzell et al. | |
| 4,450,227 A | 5/1984 | Holmes et al. | |
| 5,151,520 A | 9/1992 | Gottschalk et al. | |
| 6,218,076 B1 | 4/2001 | Ogata et al. | |
| 6,919,291 B2 | 7/2005 | Rodriguez | |
| 7,629,125 B2 | 12/2009 | Sood et al. | |
| 7,741,046 B2 | 6/2010 | Larsen et al. | |
| 8,568,991 B2 | 10/2013 | Natarajan et al. | |
| 2008/0032321 A1 | 2/2008 | Ginty et al. | |
| 2008/0032328 A1 | 2/2008 | Cline et al. | |
| 2008/0033657 A1 | 2/2008 | Cline et al. | |
| 2013/0178392 A1 | 7/2013 | Sood et al. | |
| 2014/0024024 A1 | 1/2014 | Sood et al. | |

FOREIGN PATENT DOCUMENTS

| | | |
|---|---|---|
| WO | 1997021737 A1 | 6/1997 |
| WO | 2014093455 A1 | 6/2014 |
| WO | 2014099222 A1 | 6/2014 |

OTHER PUBLICATIONS

Schuster et al.,"Photo-initiated electron transfer reactions in dye-borate ion pairs: energy, distance and solvent dependence", Journal of Photochemistry and Photobiology A: Chemistry, ScienceDirect, vol. 65, Issues 1-2, pp. 191-196, Apr. 30, 1992.
Deerinck et al.,"Fluorescence photooxidation with eosin: a method for high resolution immunolocalization and in situ hybridization detection for light and electron microscopy", J Cell Biol., 126(4):901-10, Aug. 1994.
Lambert et al.,"Cationic π-electron systems with high quadratic hyperpolarisability", Journal of the Chemical Society, Perkin Transactions 2,Issue 6, 964-974, 2001.
Lambert et al.,"Polarized π-Electron Systems in a Chemically Generated Electric Field: Second-Order Nonlinear Optical Properties of Ammonium/Borate Zwitterions", Angewandte Chemie International Edition in English, vol. 35 Issue 6, pp. 644-646, Apr. 1, 1996.
Chatterjee et al., "Photochemistry of carbocyanine alkyltriphenylborate salts: intra-ion-pair electron transfer and the chemistry of boranyl radicals", Journal of the American Chemical Society, 112 (17), pp. 6329-6338, Aug. 1990.
Natarajan et al., "Methods of Analyzing an H&E Stained Biological Sample", U.S. Appl. No. 13/786,747, filed Mar. 6, 2013.
Gerdes et al.,"Highly multiplexed single-cell analysis of formalin-fixed, paraffin-embedded cancer tissue", PNAS, vol. 110 (29), pp. 11982-11987, Jul. 16, 2013.
Ellis, "Hematoxylin and Eosin (H&E) Staining Protocol", http://www.ihcworld.com/_protocols/special_stains/h&e_ellis.htm, IHCWorld.com Website.
Arunkumar Natarajan et al., Feb. 13, 2015, U.S. Appl. No. 14/621,776.

*Primary Examiner* — Kaijiang Zhang
(74) *Attorney, Agent, or Firm* — GE Global Patent Operation; Pabitra Chakrabarti

(57) ABSTRACT

Methods comprising the use of photoactivated chemical bleaching for detecting multiple targets in a biological sample are provided. The methods include the steps of providing a biological sample containing multiple targets, binding at least one probe to one or more target present in the sample, and observing a signal from the probe. The method further includes the steps of contacting the sample comprising the bound probe with a cationic or zwitterionic borate compound and irradiating the sample, thereby initiating a photoreaction that substantially inactivates the probe by photoactivated chemical bleaching. The method further includes the steps of binding at least one probe to one or more target present in the sample, and observing a signal from the probe. The process of binding, observing and bleaching may be iteratively repeated.

29 Claims, 13 Drawing Sheets (a)

(b)

(c)

(d)

(e)

(a)

(b)

(a)

(b)

(a)          (b)

PHOTOACTIVATED CHEMICAL BLEACHING OF DYES USING BORATES

CROSS-REFERENCE TO RELATED APPLICATIONS

This application is related to U.S. patent application entitled "Borates for Photoactivated Chemical Bleaching" filed concurrently herewith under Ser. No. 14/621,776; the entire disclosure is incorporated herein by reference.

BACKGROUND

Various methods may be used in biology and in medicine to observe different targets in a biological sample. For example, analysis of proteins in histological sections and other cytological preparations may be performed using the techniques of histochemistry, immunohistochemistry (IHC), or immunofluorescence. Analysis of proteins in biological samples may also be performed using solid-state immunoassays, for example, using the techniques of western blots, or using cell-based assays that can be performed, for example, by using flow cytometry.

Many of the current techniques may detect only a few targets at one time (such as IHC or fluorescence-based Western blots where number of targets detectable is limited by the fluorescence-based detection system) in a single sample. Further analysis of targets may require use of additional biological samples from the source, limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis.

Methods of iteratively analyzing an individual sample are described in U.S. Pat. Nos. 7,629,125 and 7,741,046. In particular, U.S. Pat. No. 7,741,046 provides methods of detecting multiple targets in a biological sample that involve the use of oxidation for inactivating signal generators (e.g., for bleaching fluorescent dyes.) The oxidation reaction is accomplished by using oxidizing reagents, such as hydrogen peroxide. Furthermore U.S. Pat. No. 8,568,991 issued Oct. 29, 2013 and U.S. patent application Ser. No. 13/786,747 filed Mar. 6, 2013 shows, a signal can be inactivated by continuous exposure of the signal generator to irradiation, i.e., by photobleaching using anionic borates having a cationic counter ion.

However anionic borates, with a cationic counter ion, while they perform well, are not as efficient as desired for probes with a xanthene class of dyes. They also show high susceptibility to oxidation and often require special storage and handling protocols. As such a class of borates which are stable to oxidation and which can perform in a similar fashion in iterative staining especially to rapidly bleach xanthene dyes is desirable.

BRIEF DESCRIPTION

Disclosed herein are novel methods for high-throughput multiplex sample analysis. The methods employ, e.g., a signal cycling process wherein in each cycle, a photo-induced chemical bleaching (PICB) step allows the same signal generators, e.g., fluorophores, to be reused in the subsequent cycle to detect additional markers, e.g., proteins. These methods can be employed, e.g., for sequentially analyzing a biological sample to discern, among other things, the presence, absence, concentration, and/or spatial distribution of multiple biological targets in a biological sample. The PICB step can include applying a borate compound of Formula I, which acts as an electron transfer agent, and initiating a photoreaction, e.g., by irradiating the sample with visible light, to inactivate the signal generator, e.g., fluorescent dye.

In some embodiments, the present invention is a method of probing multiple targets in a biological sample comprising:

(a) providing a biological sample containing multiple targets;
(b) binding at least one probe to one or more targets present in the sample;
(c) observing a signal from the at least one probe bound in step (b);
(d) contacting the sample comprising the bound probe of step (b) with a borate compound of Formula I;

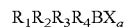

where each $R_1$, $R_2$, and $R_3$ and $R_4$ is, independently, an alkyl, an alkylaryl, an arylalkyl, or an aryl, with the proviso that at least one of $R_1$, $R_2$, and $R_3$ and $R_4$ is an alkyl group and at least one of $R_1$, $R_2$, and $R_3$ and $R_4$ group is positively charged;
X is an anion; and
a equals 0, 1, 2, or 3
(e) irradiating the sample of step (d) and
(f) analyzing the sample for one or more targets.

In some embodiments, the probe in step (b) comprises an optical signal generator, and the signal observed in step (c) is an optical signal. In further embodiments, the optical signal generator is a fluorescent signal generator, and the optical signal observed in step (c) is a fluorescent signal.

In some embodiments, step (b) includes binding more than one probe to two or more targets. In certain embodiments step (b) may involve multiple probes to the same target.

In some embodiments, the present invention is a method of probing multiple targets in a biological sample comprising:

(a) providing a biological sample containing multiple targets;
(b) binding multiple probes to multiple targets present in the sample;
(c) observing a first set of signals from the first set of probes bound in step (b);
(d) contacting the sample comprising the bound probes of step (b) with a borate compound of Formula I;

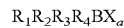

where each $R_1$, $R_2$, and $R_3$ and $R_4$ is, independently, an alkyl, an alkylaryl, an arylalkyl, or an aryl, with the proviso that at least one of $R_1$, $R_2$, and $R_3$ and $R_4$ is an alkyl group and at least one of $R_1$, $R_2$, and $R_3$ and $R_4$ group is positively charged;
X is an anion; and
a equals 0, 1, 2, or 3;
(e) irradiating the sample of step (d);
(f) generating a second set of signals from the second set of probes bound in step (b);
(g) observing the second set of signals.

In some embodiments, the present invention is a series of at least two images depicting optically labeled biological targets. The images are obtained in the process of probing multiple targets in a biological sample, wherein the process comprises:

(a) providing a biological sample containing multiple targets;
(b) binding at least one optical probe to one or more targets present in the sample;
(c) capturing a first image a signal from the optical probe bound in step (b)
(d) contacting the sample comprising the bound optical probe of step (b) with a borate compound of Formula I;

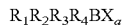

where each $R_1$, $R_2$, and $R_3$ and $R_4$ is, independently, an alkyl, an alkylaryl, an arylalkyl, or an aryl, with the proviso that at least one of $R_1$, $R_2$, and $R_3$ and $R_4$ is an alkyl group and at least one of $R_1$, $R_2$, and $R_3$ and $R_4$ group is positively charged;
X is an anion; and
a equals 0, 1, 2, or 3;
(e) irradiating the sample of step (d);
(f) binding at least one optical probe to one or more targets present in the sample of step (e); and
(g) capturing a subsequent image a signal from the optical probe bound in step (f).

DETAILED DESCRIPTION

Figure 1:
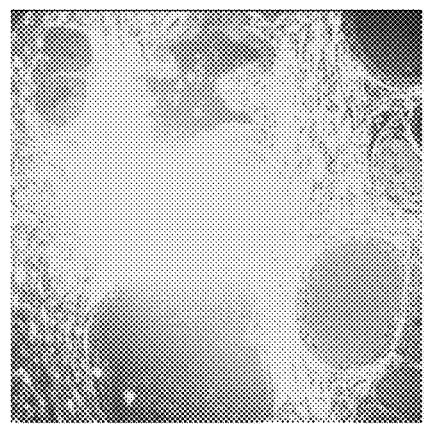
FIG. 1 are micrographs showing cationic borates efficiently bleach eosin in tissues by photoactivated bleaching with f': (a) tissue with residual eosin stain, (b) after bleaching with the borate f', (c) viewing the bleached sample after staining with PCK26 in the same channel, (d) and (e) the corresponding non-H&E staining controls.
Figure 1:
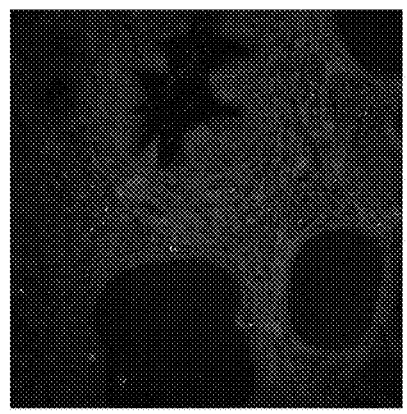
Figure 1:
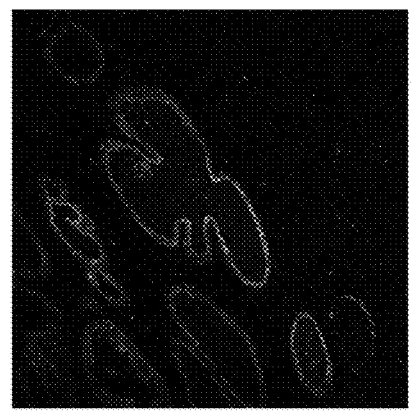
Figure 1:
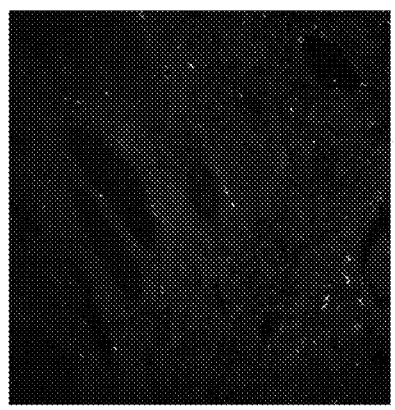
Figure 1:
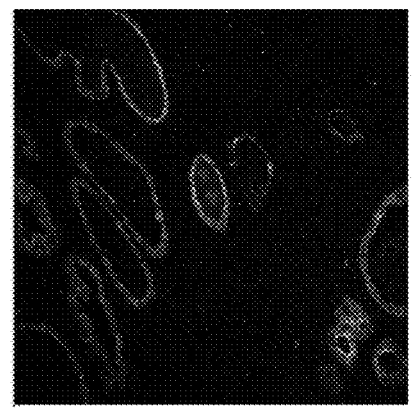

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein, the term "alkyl" refers to saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.) and cyclic alkyl groups. In certain embodiments, a straight chain or branched chain alkyl has 6 or fewer carbon atoms in its backbone (e.g., $C_1$-$C_6$ for straight chain, $C_3$-$C_6$ for branched chain) or 4 or fewer carbon atoms in its backbone (e.g., $C_1$-$C_4$ for straight chain, $C_3$-$C_4$ for branched chain). The term "$C_1$-$C_6$" alkyl refers to alkyl groups containing 1 to 6 carbon atoms. The term "$C_1$-$C_4$" alkyl refers to alkyl groups containing 1 to 4 carbon atoms. Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, (C1-C4)alkyl, (C1-C4)alkoxy, amino (including (C1-C4) alkylamino and (C1-C4)dialkylamino), hydroxyl, cyano, halogen, or nitro. Cycloalkyls can be further substituted, e.g., with the substituents described above.

As used herein, the term "alkenyl" refers to unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups. Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, (C1-C4)alkyl, (C1-C4)alkoxy, amino (including (C1-C4)alkylamino and (C1-C4)dialkylamino), hydroxyl, cyano, halogen, or nitro.

As used herein, the term "alkynyl" refers to unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), or branched-chain alkynyl groups. Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, (C1-C4)alkyl, (C1-C4)alkoxy, amino (including (C1-C4)alkylamino and (C1-C4)dialkylamino), hydroxyl, cyano, halogen, or nitro.

As used herein, the term "alkoxy" refers to substituted and unsubstituted alkyl, alkenyl, and alkynyl groups covalently linked to an oxygen atom. Examples of alkoxy groups include, but are not limited to, methoxy, ethoxy, isopropyloxy, propoxy, butoxy, and pentoxy groups. In certain embodiments, a straight chain or branched chain alkoxy has 4 or fewer carbon atoms in its backbone (e.g., $C_1$-$C_4$ for straight chain, $C_3$-$C_4$ for branched chain). The term "$C_1$-$C_4$" alkyl refers to alkyl groups containing 1 to 4 carbon atoms As used herein, the term "amine" or "amino" refers to compounds or substituents where a nitrogen atom is covalently bonded to at least one carbon or hydrogen. The term includes "alkyl amino" which comprises groups and compounds wherein: the nitrogen is bound to at least one additional alkyl group. The term "dialkyl amino" includes groups wherein: the nitrogen atom is bound to at least two additional alkyl groups. In certain embodiments, these alkyl groups have 4 or fewer carbon atoms in their backbone (e.g., $C_1$-$C_4$ for straight chain, $C_3$-$C_4$ for branched chain). The term (C1-C4)alkylamino refers to groups and compounds, wherein the nitrogen is bound to at least one additional C1-C4 alkyl group. The term "(C1-C4)dialkylamino refers to groups and compounds, wherein the nitrogen is bound to at least two additional C1-C4 alkyl groups.

As used herein, the term "aryl" refers to groups, e.g., 5- and 6-membered single-ring aromatic groups, that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, (C1-C4)alkyl, (C1-C4)alkoxy, amino (including (C1-C4)alkylamino and (C1-C4)dialkylamino), hydroxyl, cyano, halogen, or nitro. Aryl groups can also be fused or bridged with alicyclic or heterocyclic rings which are not aromatic so as to form a polycycle (e.g., tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 1,2,3-triazole, 1,2,4, triazole, dithiazole, tetrazole, pyridine, pyran, pyrimidine, pyran, thiapyrane, diazine, thiazine, dioxine, triazine and tetrazene.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab').sub.2, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, cells isolated from mammals including, humans and cell organelles. Biological samples also may include sections of the biological sample including tissues (e.g., sectional portions of an organ or tissue). Biological samples may also include extracts from a biological sample, for example, an antigen or a nucleic acid from a biological fluid (e.g., blood or urine). Biological samples may comprise proteins, carbohydrates or nucleic acids.

As used herein, the term "control probe" refers to an agent having a binder coupled to a signal generator or a signal generator capable of staining directly, such that the signal generator retains at least 80 percent signal after contact with an electron-transfer photoinitiating reagent and subsequent irradiation. A suitable signal generator in a control probe is not substantially inactivated, e.g., substantially bleached by photoactivated chemical bleaching, when contacted with the electron-transfer photoinitiating reagent and irradiated at selected region of the spectrum. Suitable examples of signal generators may include a fluorophore that does not undergo bleaching under the conditions employed (e.g., DAPI). Fluorophores that are bleached under one irradiation wavelength can be stable when irradiated with the wavelength that is substantially outside the excitation wavelength range of that fluorophore.

As used herein, the term "enzyme" refers to a protein molecule that can catalyze a chemical reaction of a substrate. In some embodiments, a suitable enzyme catalyzes a chemical reaction of the substrate to form a reaction product that can bind to a receptor (e.g., phenolic groups) present in the sample. A receptor may be exogeneous (that is, a receptor extrinsically adhered to the sample or the solid-support) or endogeneous (receptors present intrinsically in the sample or the solid-support) (What is the definition of receptor? Enzyme reactions generally generate products that are reactive, for example radicals or anions, precipitates or soluble products that may be measured as they are produced or captured due to hydrophobic nature of the product that makes it stick to the sample or by a biological receptor). Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase.

As used herein, the term "enzyme substrate" refers to a chemical compound that is chemically catalyzed by an enzyme to form a reaction product. In some embodiments, the reaction product is capable of binding to a receptor present in the sample. In some embodiments, enzyme substrates employed in the methods herein may include non-chromogenic or non-chemiluminescent substrates. A signal generator may be attached to the enzyme substrate as a label.

As used herein, the term "electron-transfer photoinitiating reagent" refers to a reagent that can engage in a photoreaction with a molecule capable of undergoing photoexcitation. This term also refers to a composition comprising a reagent that can engage in a photoreaction with a molecule capable of undergoing photoexcitation. In some embodiments, the molecule capable of undergoing photoexcitation may be a signal generator. In some embodiment, the electron-transfer photoinitiating reagent may donate an electron to the signal generator in the course of a photoreaction. In alternative embodiments, the electron-transfer photoinitiating reagent may accept an electron from the signal generator in the course of a photoreaction.

In some embodiments, the electron-transfer photoinitiating reagent donating an electron to the signal generator in the course of a photoreaction may be a borate compound of Formula I:

$$R_1R_2R_3R_4BX_a \qquad \text{I}$$

where each $R_1$, $R_2$, and $R_3$ and $R_4$ is, independently, an alkyl, an alkylaryl, an arylalkyl, or an aryl, with the proviso that at least one of $R_1$, $R_2$, and $R_3$ and $R_4$ is an alkyl group and at least one of $R_1$, $R_2$, and $R_3$ and $R_4$ group is positively charged;

X is an anion; and a equals 0, 1, 2, or 3.

As used herein, the term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5''-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, cyanines, pyrelium dyes, squaraines, 1,3-dichloro-7-hydroxy-9,9-dimethyl-2(9H)-

Acridinone (DDAO), and dimethylacridinone (DAO). In some embodiments, the fluorophore can be cyanine, rhodamine, BODIPY or 1,3-dichloro-7-hydroxy-9,9-dimethyl-2 (9H)-Acridinone (DDAO) dyes. In a preferred embodiment, the fluorophore is a cyanine dye. In a further embodiment, the cyanine dye is Cy3 or Cy5.

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the terms "irradiation" or "irradiate" refer to act or process of exposing a sample or a solution to non-ionizing radiation. In some embodiments, the non-ionizing irradiation has wavelengths between 350 nm and 1.3 µm. In preferred embodiments, the non-ionizing radiation is visible light of 400-700 nm in wavelength. In most preferred embodiments, the non-ionizing radiation is visible light in the range of 500-650 nm. Irradiation may be accomplished by exposing a sample or a solution to a radiation source, e.g., a lamp, capable of emitting radiation of a certain wavelength or a range of wavelengths. As such the term "exposure to light" refers to irradiation. In some embodiments, a molecule capable of undergoing photoexcitation is photoexcited as a result of irradiation. In some embodiments, the molecule capable of undergoing photoexcitation is a signal generator, e.g., a fluorescent signal generator. In some embodiments, irradiation of a fluorescent signal generator initiates a photoreaction between the fluorescent signal generator and the electron-transfer photoinitiating reagent. In some embodiments, irradiation initiates a photoreaction substantially inactivates the signal generator by photoactivated chemical bleaching.

Optical filters may be used to restrict irradiation of a sample or a solution to a particular wavelength or a range of wavelengths. In some embodiments, the optical filters may be used to restrict irradiation to a narrow range of wavelengths for selective photoexcitation of one or more molecules capable of undergoing photoexcitation. The term "selective photoexcitation" refers to an act or a process, whereby one or more molecules capable of undergoing photoexcitation are photoexcited in the presence of one or more other molecules capable of undergoing photoexcitation that remain in the ground electronic state after irradiation and don't bleach under the conditions employed.

In some embodiments, the molecule capable of undergoing photoexcitation is a fluorescent dye, e.g., a cyanine dye. In one further embodiment, irradiation limited to a range of wavelengths between 520-580 nm is used for selective photoexciation of a Cy3 dye. In another further embodiment, irradiation limited to a range of wavelengths between 620-680 nm is used for selective photoexcitation of a Cy5 dye. In preferred embodiments, irradiation of a sample at a specific wavelength is accomplished by using a laser.

As used herein, the term "peroxidase" refers to an enzyme class that catalyzes an oxidation reaction of an enzyme substrate along with an electron donor. Examples of peroxidase enzymes include horseradish peroxidase, cytochrome C peroxidase, glutathione peroxidase, microperoxidase, myeloperoxidase, lactoperoxidase, or soybean peroxidase.

As used herein, the term "peroxidase substrate" refers to a chemical compound that is chemically catalyzed by peroxidase to form a reaction product. In some embodiments, peroxidase substrates employed in the methods herein may include non-chromogenic or non-chemiluminescent substrates. A fluorescent signal generator may be attached to the peroxidase substrate as a label.

As used herein, the term "bleaching", "photoactivated chemical bleaching" or "photoinduced chemical bleaching" refers to an act or a process whereby a signal generated by a signal generator is modified in the course of a photoreaction initiated by electron transfer. In certain embodiments, the signal generator is irreversibly modified.

In some embodiments, the signal is diminished or eliminated as a result of photoactivated chemical bleaching. In some embodiments, the signal generator is completely bleached, i.e., the signal intensity decreases by about 100%. In some embodiments, the signal is an optical signal, and the signal generator is an optical signal generator. The term "photoactivated chemical bleaching" is meant to exclude photobleaching, or loss of signal (e.g., fluorescent signal) that may occur in the absence of electron-transfer photoinitiating reagent, e.g., after continued irradiation of a signal generator, such as a fluorophore, or after its continued exposure to light.

As used herein, the term "photoexcitation" refers to an act or a process whereby a molecule transitions from a ground electronic state to an excited electronic state upon absorption of radiation energy, e.g. upon irradiation. Photoexcited molecules can participate in chemical reactions, e.g., in electron transfer reactions. In some embodiments, a molecule capable of undergoing photoexcitation is a signal generator, e.g., a fluorescent signal generator.

As used herein, the term "photoreaction" or a "photoinduced reaction" refers to a chemical reaction that is initiated and/or proceeds as a result of photoexcitation of at least one reactant. The reactants in a photoreaction may be an electron-transfer photoinitiating reagent and a molecule capable of undergoing photoexcitation. In some embodiments, a photoreaction may involve an electron transfer from the electron-transfer photoinitiating reagent to the molecule that has undergone photoexcitation, i.e., the photoexcited molecule. In alternative embodiments, a photoreaction may also involve an electron transfer from the molecule that has undergone photoexcitation to the electron-transfer photoinitiating reagent. In some embodiments, the molecule capable of undergoing photoexcitation is a fluorescent signal generator, e.g., a fluorophore. In some embodiments, photoreaction results in irreversible modification of one or more components of the photoreaction. In some embodiments, photoreaction substantially inactivates the signal generator by photoactivated chemical bleaching.

In some embodiments, the photoreaction may involve in intermolecular electron transfer between the electron-transfer photoinitiating reagent and the photoexcited molecule, e.g., the electron transfer occurs when the association between the electron-transfer photoinitiating reagent and the photoexcited molecule is transitory, occurring just prior to the electron transfer and ceasing after electron transfer.

In some embodiments, the photoreaction may involve intramolecular electron transfer between the electron-transfer photoinitiating reagent and the photoexcited molecule, e.g. the electron transfer occurs when the electron-transfer photoinitiating reagent and the photoexcited molecule have been linked together, e.g., by covalent or electrostatic interactions, prior to initiation of the electron transfer process. The photoreaction involving the intramolecular electron transfer can occur, e.g., when the molecule capable of undergoing photoexcitation and the electron-transfer photoinitiating reagent carry opposite charges and form a complex held by electrostatic interactions. For example in certain embodiments, an anionic dye, e.g., an anionic xanthene dye such as fluorescein or eosin and the borate compound of Formula I may form a complex, wherein intramolecular electron transfer may occur between the xanthene dye and borate moieties upon irradiation.

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator. In some embodiments, the probe may comprise an optical signal generator, such that the signal observed is an optical signal. In some embodiments, the probe may comprise a fluorescent signal generator, such that the signal observed is a fluorescent signal.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal. Examples of signal generators include one or more of a chromophore, a fluorophore, or a Raman-active tag. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

In some embodiments, the signal generator may be an optical signal generator. In some embodiments, the optical signal generator may be a fluorescent signal generator, e.g., a fluorophore. In preferred embodiments, the fluorescent signal generator may be a cyanine dye, e.g., Cy2, Cy3, Cy5 or Cy7. In some embodiments, the signal generator, e.g., a fluorophore, may be charged. In one embodiment, the signal generator is a cationic fluorescent dye. In other embodiments, the signal generator is an anionic fluorescent dye.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant ($K_A$) for the target no lower than about $10^5$ $M^{-1}$ under ambient conditions such as a pH of about 6 to about 8 and temperature ranging from about 0° C. to about 37° C.

As used herein, the term "target" refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

The invention includes embodiments that relate generally to methods applicable in analytical, diagnostic, or prognostic applications such as analyte detection, fluorescence-activated cell sorting (FACS), histochemistry, immunohistochemistry, immunofluorescence, or fluorescence in situ hybridization (FISH). In some embodiments, the methods disclosed herein may be particularly applicable in histochemistry, immunostaining, immunohistochemistry, immunoassays, immunofluorescence or FISH. In some embodiments, the methods disclosed herein may be particularly applicable in immunoblotting techniques, for example, western blots or immunoassays such as enzyme-linked immunosorbent assays (ELISA).

The disclosed methods relate generally to detection of multiple targets in a single biological sample. In some embodiments, methods of detecting multiple targets in a single biological sample using the same detection channel are disclosed. The targets may be present on the surface of cells in suspension, on the surface of cytology smears, on the surface of histological sections, on the surface of DNA microarrays, on the surface of protein microarrays, or on the surface of solid supports (such as gels, blots, glass slides, beads, or ELISA plates).

The methods disclosed herein may allow detection of a plurality of targets in the same biological sample with little or no effect on the integrity of the biological sample. Detecting the targets in the same biological sample may further provide spatial information about the targets in the biological sample. Methods disclosed herein may also be applicable in analytical applications where a limited amount of biological sample may be available for analysis and the same sample may have to be processed for multiple analyses. Methods disclosed herein may also facilitate multiple analyses of solid-state samples (e.g., tissue sections) or samples adhered to a solid support (e.g., blots) without substantially stripping the probes and the targets. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about four as only about four fluorescent signals may be resolvable based on their excitation and emission wavelength properties. In some embodiments, the methods disclosed herein may allow detection of greater than four targets using fluorescent-based detection system.

In some embodiments, the method is a high throughput multiplexing biological sample analysis that includes a signal cycling process, wherein in each cycle, staining and imaging is followed by applying a borate compound, which acts as an electron-transfer photoinitiating reagent, and irradiation of the biological sample. The method allows rapid signal cycling without significantly modifying the components of the biological sample that are different from the probe.

In some embodiments, the method of detecting multiple targets in a biological sample includes sequential detection of targets in the biological sample. The method generally includes the steps of detecting a first set of targets in the biological sample, bleaching the signal from the first set of targets by photoinduced chemical bleaching. In some embodiments, the method further includes detecting a second set of targets in the biological sample. The method may further include repeating the step of photoinduced chemical bleaching of signal from the second set of targets, followed by detecting a third set of targets in the biological sample, and so forth.

In some embodiments, the method includes the steps of contacting a biological sample with a first probe and physically binding a first probe to a first target. The method further includes observing a first signal from the first probe. An electron-transfer photoinitiating reagent is applied to the probe, and the sample containing the electron-transfer photoinitiating reagent and the probe is irradiated, thereby initiating a photoreaction that modifies the first signal. The method further includes contacting the biological sample with a second probe and physically binding the second probe to a second target in the biological sample followed by observing a second signal from the second probe.

In some embodiments, the method also includes the steps of contacting a biological sample with a plurality of multiple sets of probes and physically binding the plurality of probes to a plurality of targets. The method further includes observing a first set of signals from the first set of the plurality of probes. An electron-transfer photoinitiating reagent is applied to the plurality of probes, and the sample is irradiated, thereby initiating a photoreaction that modifies the first set of signals from the first set of the plurality of probes. The method further includes generating the second set of signals from the second set of the plurality of targets and observing the second set of signals. Generation of the second set of signals may comprise associating the second set of probes with a separate moiety that comprises signal generator. For example, the second set of probes may comprise a biotin tag, and the moiety comprising signal generator may also comprise streptavidin capable of binding the biotin tag. Alternatively, generation of the second set of signals may comprise un-masking the signal-generating moiety, e.g., by modifying the distance between the fluorophore-quencher pair. In yet another embodiment, the second set of signals may arise from hybridization of labeled nucleic acid probes to unlabeled complementary sequences on the second set of probes.

In other embodiments, the method includes the steps of providing a sample containing multiple targets and binding at least one probe having a binder coupled to an enzyme to one or more target present in the sample. The method further includes reacting the bound probe with an enzyme substrate coupled to a signal generator and observing a signal from the signal generator. An electron-transfer photoinitiating reagent that substantially inactivates both the signal generator and the enzyme in the course of a photoreaction is applied to the sample. The method also includes an optional separate step of inactivating the enzyme. The step of enzyme inactivation may comprise, e.g., application of an enzyme inactivation reagent. The method further includes binding at least one subsequent probe having a binder coupled to an enzyme to one or more target present in the sample. The method further includes reacting the bound probe with an enzyme substrate coupled to a signal generator and observing a signal from the signal generator.

In yet other embodiments, the method includes the steps of providing a biological sample containing multiple targets and binding at least one probe to one or more target present in the sample. The method further includes observing a signal from the bound probe. The bound probe is contacted with an electron-transfer photoinitiating reagent, and the sample comprising the bound probe and the electron-transfer photoinitiating reagent is irradiated, thereby bleaching the probe. The method further includes binding at least one subsequent probe to one or more target present in the sample followed by observing a signal from the subsequent bound probe.

In yet other embodiments, the method includes the steps of providing a biological sample containing multiple targets and binding at least one fluorescent probe to one or more target present in the sample. The method further includes binding at least one control probe to one or more target in the sample. The bound probe is contacted with an electron-transfer photoinitiating reagent, and the sample comprising the bound probe and the electron-transfer photoinitiating reagent is irradiated, thereby bleaching the probe and not the control probe. The method further includes binding at least one subsequent probe to one or more target present in the sample followed by observing a signal from the subsequent bound probe.

In yet other embodiments, the methods described above provide a series of at least two images depicting optically labeled biological targets.

Biological Samples

A biological sample in accordance with one embodiment of the invention may be solid or fluid. Suitable examples of biological samples may include, but are not limited to, cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. Cell cultures may include mixed cell culture, stem cell colonies or cultures derived from various cancer or primary cell lines. In some embodiments, the biological sample may be analyzed as is, that is, without harvest and/or isolation of the target of interest. In an alternative embodiment, harvesting and isolation of targets may be performed prior to analysis. In some embodiments, the methods disclosed herein may be particularly suitable for in vitro analysis of biological samples.

A biological sample may include any of the aforementioned samples regardless of their physical condition, such as, but not limited to, being frozen or stained or otherwise treated. In some embodiments, a biological sample may include compounds which are not naturally intermixed with the sample in nature such as preservatives, anticoagulants, buffers, fixatives, nutrients, antibiotics, or the like.

In some embodiments, a biological sample may include a tissue sample or section, a whole cell, a cell constituent, e.g., cell organelle, a cytospin, or a cell smear. In some embodiments, a biological sample essentially includes a tissue sample. A tissue sample may include a collection of similar cells obtained from a tissue of a biological subject that may have a similar function. In some embodiments, a tissue sample may include a collection of similar cells obtained from a tissue of a human. Suitable examples of human tissues include, but are not limited to, (1) epithelium; (2) the connective tissues, including blood vessels, bone and cartilage; (3) muscle tissue; and (4) nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a biological sample includes tissue sections from healthy or diseased tissue samples (e.g., tissue section from colon, breast tissue, prostate). A tissue section may include a single part or piece of a tissue sample, for example, a thin slice of tissue or cells cut from a tissue sample. In some embodiments, multiple sections of tissue samples may be taken and subjected to analysis, provided the methods disclosed herein may be used for analysis of the same section of the tissue sample with respect to at least two different targets (at morphological or molecular level). In some embodiments, tissue microarray may be used. In some embodiments, the same section of tissue sample may be analyzed with respect to at least four different targets (at morphological or molecular level). In some embodiments, the same section of tissue sample may be analyzed with respect to greater than four different targets (at morphological or molecular level). In some embodiments, the same section of tissue sample may be analyzed at both morphological and molecular levels.

A tissue section, if employed as a biological sample may have a thickness in a range that is less than about 100 micrometers, in a range that is less than about 50 micrometers, in a range that is less than about 25 micrometers, in range that is less than about 10 micrometers, in a range that is less than 5 micrometer or in a range that is less than 2 um.

In some embodiments, the biological sample may comprise one or more of proteins, carbohydrates or nucleic acids. In some embodiments, a biological sample or the targets in the biological sample may be adhered to a solid support. A solid support may include microarrays (e.g., DNA or RNA microarrays), gels, blots, glass slides, beads, or ELISA plates. In some embodiments, a biological sample or the targets in the biological sample may be adhered to a membrane selected from nylon, nitrocellulose, and polyvinylidene difluoride. In some embodiments, the solid support may include a plastic surface selected from polystyrene, polycarbonate, and polypropylene.

Targets

A target may be present on the surface of a biological sample (for example, an antigen on a surface of a tissue section) or present in the bulk of the sample (for example, an antibody in a buffer solution). In some embodiments, a target may not be inherently present on the surface of a biological sample and the biological sample may have to be processed to make the target available on the surface (e.g., antigen recovery, enzymatic digestion, epitope retrieval, or blocking) In some embodiments, the target may be present in a body fluid such as blood, blood plasma, serum, or urine. In some other embodiments, the target may be fixed in a tissue, either on a cell surface, or within a cell.

Suitability of targets to be analyzed may be determined by the type and nature of analysis required for the biological sample. In some embodiments, a target may provide information about the presence or absence of an analyte in the biological sample. In another embodiment, a target may provide information on a state of a biological sample. For example, if the biological sample includes a tissue sample, the methods disclosed herein may be used to detect targets that may help in comparing different types of cells or tissues, comparing different developmental stages, detecting the presence of a disease or abnormality, or determining the type of disease or abnormality.

Targets may include one or more of peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may essentially include proteins or nucleic acids. In other embodiments, multiple types of targets, e.g., nucleic acids, polysaccharides, lipids, enzymes, enzyme substrates, ligands, receptors, antigens or haptens may be detected and/or analyzed in the same biological sample in one or multiple cycles. One or more of the aforementioned targets may be characteristic of particular cells, while other targets may be associated with a particular disease or condition. In some embodiments, targets that may be detected and analyzed using the methods disclosed herein may include, but are not limited to, prognostic targets, hormone or hormone receptor targets, lymphoid targets, tumor targets, cell cycle associated targets, neural tissue and tumor targets, or cluster differentiation targets.

Suitable examples of prognostic targets may include enzymatic targets such as galactosyl transferase II, neuron specific enolase, proton ATPase-2, or acid phosphatase.

Suitable examples of hormone or hormone receptor targets may include human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, or insulin receptor.

Suitable examples of lymphoid targets may include alpha-1-antichymotrypsin, alpha-1-antitrypsin, B cell target, bcl-2, bcl-6, B lymphocyte antigen 36 kD, BM1 (myeloid target), BM2 (myeloid target), galectin-3, granzyme B, HLA class I Antigen, HLA class II (DP) antigen, HLA class II (DQ) antigen, HLA class II (DR) antigen, human neutrophil defensins, immunoglobulin A, immunoglobulin D, immunoglobulin G, immunoglobulin M, kappa light chain, kappa light chain, lambda light chain, lymphocyte/histocyte antigen, macrophage target, muramidase (lysozyme), p80 anaplastic lymphoma kinase, plasma cell target, secretory leukocyte protease inhibitor, T cell antigen receptor (JOVI 1), T cell antigen receptor (JOVI 3), terminal deoxynucleotidyl transferase, or unclustered B cell target.

Suitable examples of tumor targets may include alpha fetoprotein, apolipoprotein D, BAG-1 (RAP46 protein), CA19-9 (sialyl lewisa), CA50 (carcinoma associated mucin antigen), CA125 (ovarian cancer antigen), CA242 (tumour associated mucin antigen), chromogranin A, clusterin (apolipoprotein J), epithelial membrane antigen, epithelial-related antigen, epithelial specific antigen, gross cystic disease fluid protein-15, hepatocyte specific antigen, heregulin, human gastric mucin, human milk fat globule, MAGE-1, matrix metalloproteinases, melan A, melanoma target (HMB45), mesothelin, metallothionein, microphthalmia transcription factor (MITF), Muc-1 core glycoprotein. Muc-1 glycoprotein, Muc-2 glycoprotein, Muc-5AC glycoprotein, Muc-6 glycoprotein, myeloperoxidase, Myf-3 (Rhabdomyosarcoma target), Myf-4 (Rhabdomyosarcoma target), MyoD1 (Rhabdomyosarcoma target), myoglobin, nm23 protein, placental alkaline phosphatase, prealbumin, prostate specific antigen, prostatic acid phosphatase, prostatic inhibin peptide, PTEN, renal cell carcinoma target, small intestinal mucinous antigen, tetranectin, thyroid transcription factor-1, tissue inhibitor of matrix metalloproteinase 1, tissue inhibitor of matrix metalloproteinase 2, tyrosinase, tyrosinase-related protein-1, villin, or von Willebrand factor.

Suitable examples of cell cycle associated targets may include apoptosis protease activating factor-1, bcl-w, bcl-x, bromodeoxyuridine, CAK (cdk-activating kinase), cellular apoptosis susceptibility protein (CAS), caspase 2, caspase 8, CPP32 (caspase-3), CPP32 (caspase-3), cyclin dependent kinases, cyclin A, cyclin B1, cyclin D1, cyclin D2, cyclin D3, cyclin E, cyclin G, DNA fragmentation factor (N-terminus), Fas (CD95), Fas-associated death domain protein, Fas ligand, Fen-1, IPO-38, Mcl-1, minichromosome maintenance proteins, mismatch repair protein (MSH2), poly (ADP-Ribose) polymerase, proliferating cell nuclear antigen, p16 protein, p27 protein, p34cdc2, p57 protein (Kip2), p105 protein, Stat 1 alpha, topoisomerase I, topoisomerase II alpha, topoisomerase III alpha, or topoisomerase II beta.

Suitable examples of neural tissue and tumor targets may include alpha B crystallin, alpha-internexin, alpha synuclein, amyloid precursor protein, beta amyloid, calbindin, choline acetyltransferase, excitatory amino acid transporter 1, GAP43, glial fibrillary acidic protein, glutamate receptor 2, myelin basic protein, nerve growth factor receptor (gp75), neuroblastoma target, neurofilament 68 kD, neurofilament 160 kD, neurofilament 200 kD, neuron specific enolase, nicotinic acetylcholine receptor alpha4, nicotinic acetylcholine receptor beta2, peripherin, protein gene product 9, S-100 protein, serotonin, SNAP-25, synapsin I, synaptophysin, tau, tryptophan hydroxylase, tyrosine hydroxylase, or ubiquitin.

Suitable examples of cluster differentiation targets may include CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

Other suitable prognostic targets may include centromere protein-F (CENP-F), giantin, involucrin, lamin A&C (XB 10), LAP-70, mucin, nuclear pore complex proteins, p180 lamellar body protein, ran, r, cathepsin D, Ps2 protein, Her2-neu, P53, S100, epithelial target antigen (EMA), TdT, MB2, MB3, PCNA, or Ki67.

Probes

In some embodiments, a binder and a label (signal generator or an enzyme) may be coupled to each other directly (that is without any linkers). In other embodiments, a binder and a label (signal generator or an enzyme) may be coupled to each other via a linker. As used herein, "coupled" generally refers to two entities (for example, binder and signal generator) stably bound to one another by any physicochemical means. The nature of the coupling may be such that it does not substantially impair the effectiveness of either entity. A binder and a label may be coupled to each other through covalent or non-covalent interactions. Non-covalent interactions may include, but are not limited to, hydrophobic interactions, ionic interactions, hydrogen-bond interactions, high affinity interactions (such as, biotin-avidin or biotin-streptavidin complexation), or other affinity interactions.

In some embodiments, a binder and a label (signal generator or an enzyme) may be chemically linked to each other through functional groups capable of reacting and forming a linkage under suitable conditions. Suitable examples of functional group combinations may include, but are not limited to, amine ester and amines or anilines; acyl azide and amines or anilines; acyl halides and amines, anilines, alcohols, or phenols; acyl nitrile and alcohols or phenols; aldehyde and amines or anilines; alkyl halide and amines, anilines, alcohols, phenols or thiols; alkyl sulfonate and thiols, alcohols or phenols; anhydride and alcohols, phenols, amines or anilines; aryl halide and thiols; aziridine and thiols or thioethers; carboxylic acid and amines, anilines, alcohols or alkyl halides; diazoalkane and carboxylic acids; epoxide and thiols; haloacetamide and thiols; halotriazin and amines, anilines or phenols; hydrazine and aldehydes or ketones; hydroxyamine and aldehydes or ketones; imido ester and amines or anilines; isocyanate and amines or anilines; and isothiocyanate and amines or anilines. A functional group in one of the aforementioned functional group pair may be present in a binder and a corresponding functional group may be present in the signal generator or the enzyme. For example, a binder may include a carboxylic acid and the signal generator or the enzyme may include an amine, aniline, alcohol or acyl halide, or vice versa. Conjugation between the binder and the signal generator or the enzyme may be effected in this case by formation of an amide or an ester linkage.

In some embodiments, the binder may be intrinsically labeled with a signal generator (for example, if the binder is a protein, during synthesis using a detectably labeled amino acid) or an enzyme (for example, if the binder is an enzyme). A binder that is intrinsically labeled may not require a separate signal generator or an enzyme in order to be detected. Rather the intrinsic label may be sufficient for rendering the probe detectable. In alternate embodiments, the binder may be labeled by binding to it a specific signal generator or an enzyme (i.e., extrinsically labeled).

In some embodiments, the binder and the label (signal generator or the enzyme) are embodied in a single entity. In alternative embodiments, the binder and the label (signal generator or the enzyme) are embodied in discrete entities (e.g., a primary antibody capable of binding a target and an enzyme or a signal generator-labeled secondary antibody capable of binding the primary antibody or a hapten labeled primary antibody capable of binding a target and an enzyme or a signal generator-labeled anti-hapten antibody capable of binding the hapten labeled primary antibody). When the binder and the signal generator or the enzyme are separate entities they may be applied to a biological sample in a single step or multiple steps. In some embodiments, the binder and the label (signal generator or the enzyme) are separate entities that are pre-attached before application to the biological sample and applied to the biological sample in a single step. In yet other embodiments, the binder and the label (signal generator or the enzyme) are separate entities that are applied to the biological sample independently and combine following application.

Binders

The methods disclosed herein involve the use of binders that physically bind to the target in a specific manner. In some embodiments, a binder may bind to a target with sufficient specificity, that is, a binder may bind to a target with greater affinity than it does to any other molecule. In some embodiments, the binder may bind to other molecules, but the binding may be such that the non-specific binding may be at or near background levels. In some embodiments, the affinity of the binder for the target of interest may be in a range that is at least 2-fold, at least 5-fold, at least 10-fold, or more than its affinity for other molecules. In some embodiments, binders with the greatest differential affinity may be employed, although they may not be those with the greatest affinity for the target.

In some embodiments, binding between the target and the binder may be affected by physical binding. Physical binding may include binding effected using non-covalent interactions. Non-covalent interactions may include, but are not limited to, hydrophobic interactions, ionic interactions, hydrogen-bond interactions, or affinity interactions (such as, biotin-avidin or biotin-streptavidin complexation). In some embodiments, the target and the binder may have areas on their surfaces or in cavities giving rise to specific recognition between the two resulting in physical binding. In some embodiments, a binder may bind to a biological target based on the reciprocal fit of a portion of their molecular shapes.

Binders and their corresponding targets may be considered as binding pairs, of which non-limiting examples include immune-type binding-pairs, such as, antigen/antibody, antigen/antibody fragment, or hapten/anti-hapten; nonimmune-type binding-pairs, such as biotin/avidin, biotin/streptavidin, folic acid/folate binding protein, hormone/hormone receptor, lectin/specific carbohydrate, enzyme/enzyme, enzyme/substrate, enzyme/substrate analog, enzyme/pseudo-substrate (substrate analogs that cannot be catalyzed by the enzymatic activity), enzyme/co-factor, enzyme/modulator, enzyme/inhibitor, or vitamin B12/intrinsic factor. Other suitable examples of binding pairs may include complementary nucleic acid fragments (including DNA sequences, RNA sequences, LNA sequences, and PNA sequences or other modified nucleic acids known in the literature); Protein A/antibody; Protein G/antibody; nucleic acid/nucleic acid binding protein; or polynucleotide/polynucleotide binding protein.

In some embodiments, the binder may be a sequence- or structure-specific binder, wherein the sequence or structure of a target recognized and bound by the binder may be sufficiently unique to that target.

In some embodiments, the binder may be structure-specific and may recognize a primary, secondary, or tertiary structure of a target. A primary structure of a target may include specification of its atomic composition and the chemical bonds connecting those atoms (including stereochemistry), for example, the type and nature of linear arrangement of amino acids in a protein. A secondary structure of a target may refer to the general three-dimensional form of segments of biomolecules, for example, for a protein a secondary structure may refer to the folding of the peptide "backbone" chain into various conformations that may result in distant amino acids being brought into proximity with each other. Suitable examples of secondary structures may include, but are not limited to, alpha helices, beta pleated sheets, or random coils. A tertiary structure of a target may be is its overall three dimensional structure. A quaternary structure of a target may be the structure formed by its noncovalent interaction with one or more other targets or macromolecules (such as protein interactions). An example of a quaternary structure may be the structure formed by the four-globin protein subunits to make hemoglobin. A binder in accordance with the embodiments of the invention may be specific for any of the afore-mentioned structures.

An example of a structure-specific binder may include a protein-specific molecule that may bind to a protein target. Examples of suitable protein-specific molecules may include antibodies and antibody fragments, nucleic acids (for example, aptamers that recognize protein targets), or protein substrates (non-catalyzable).

In some embodiments, a target may include an antigen and a binder may include an antibody. A suitable antibody may include monoclonal antibodies, polyclonal antibodies, multispecific antibodies (for example, bispecific antibodies), or antibody fragments so long as they bind specifically to their target antigens.

In some embodiments, a biological sample may include a cell or a tissue sample and the methods disclosed herein may be employed in immunohistochemistry (IHC). Immunochemistry may involve binding of a target antigen to an antibody-based binder to provide information about the tissues or cells (for example, diseased versus normal cells). Examples of antibodies (and the corresponding diseases/disease cells) suitable as binders for methods disclosed herein include, but are not limited to, anti-estrogen receptor antibody (breast cancer), anti-progesterone receptor antibody (breast cancer), anti-p53 antibody (multiple cancers), anti-Her-2/neu antibody (multiple cancers), anti-EGFR antibody (epidermal growth factor, multiple cancers), anti-cathepsin D antibody (breast and other cancers), anti-Bcl-2 antibody (apoptotic cells), anti-E-cadherin antibody, anti-CA125 antibody (ovarian and other cancers), anti-CA15-3 antibody (breast cancer), anti-CA19-9 antibody (colon cancer), anti-c-erbB-2 antibody, anti-P-glycoprotein antibody (MDR, multi-drug resistance), anti-CEA antibody (carcinoembryonic antigen), anti-retinoblastoma protein (Rb) antibody, anti-ras oneoprotein (p21) antibody, anti-Lewis X (also called CD15) antibody, anti-Ki-67 antibody (cellular proliferation), anti-PCNA (multiple cancers) antibody, anti-CD 3 antibody (T-cells), anti-CD4 antibody (helper T cells), anti-CD5 antibody (T cells), anti-CD7 antibody (thymocytes, immature T cells, NK killer cells), anti-CD8 antibody (suppressor T cells), anti-CD9/p24 antibody (ALL), anti-CD10 (also called CALLA) antibody (common acute lymphoblastic leukemia), anti-CD11c antibody (Monocytes, granulocytes, AML), anti-CD13 antibody (myelomonocytic cells, AML), anti-CD14 antibody (mature monocytes, granulocytes), anti-CD15 antibody (Hodgkin's disease), anti-CD19 antibody (B cells), anti-CD20 antibody (B cells), anti-CD22 antibody (B cells), anti-CD23 antibody (activated B cells, CLL), anti-CD30 antibody (activated T and B cells, Hodgkin's disease), anti-CD31 antibody (angiogenesis marker), anti-CD33 antibody (myeloid cells, AML), anti-CD34 antibody (endothelial stem cells, stromal tumors), anti-CD35 antibody (dendritic cells), anti-CD38 antibody (plasma cells, activated T, B, and myeloid cells), anti-CD 41 antibody (platelets, megakaryocytes), anti-LCA/CD45 antibody (leukocyte common antigen), anti-CD45RO antibody (helper, inducer T cells), anti-CD45RA antibody (B cells), anti-CD39, CD100 antibody, anti-CD95/Fas antibody (apoptosis), anti-CD99 antibody (Ewings Sarcoma marker, MIC2 gene product), anti-CD106 antibody (VCAM-1; activated endothelial cells), anti-ubiquitin antibody (Alzheimer's disease), anti-CD71 (transferrin receptor) antibody, anti-c-myc (oncoprotein and a hapten) antibody, anti-cytokeratins (transferrin receptor) antibody, anti-vimentins (endothelial cells) antibody (B and T cells), anti-HPV proteins (human papillomavirus) antibody, anti-kappa light chains antibody (B cell), anti-lambda light chains antibody (B cell), anti-melanosomes (HMB45) antibody (melanoma), anti-prostate specific antigen (PSA) antibody (prostate cancer), anti-S-100 antibody (melanoma, salivary, glial cells), anti-tau antigen antibody (Alzheimer's disease), anti-fibrin antibody (epithelial cells), anti-keratins antibody, anti-cytokeratin antibody (tumor), anti-alpha-catenin (cell membrane), or anti-Tn-antigen antibody (colon carcinoma, adenocarcinomas, and pancreatic cancer).

Other specific examples of suitable antibodies may include, but are not limited to, anti-proliferating cell nuclear antigen, clone pc10 (Sigma Aldrich, P8825); anti smooth muscle alpha actin (SmA), clone 1A4 (Sigma, A2547); rabbit anti beta catenin (Sigma, C2206); mouse anti pan cytokeratin, clone PCK-26 (Sigma, C1801); mouse anti estrogen receptor alpha, clone 1D5 (DAKO, M 7047); beta catenin antibody, clone 15B8 (Sigma, C7738); goat anti vimentin (Sigma, V4630); cycle androgen receptor clone AR441 (DAKO, M3562); Von Willebrand Factor 7, keratin 5, keratin 8/18, e-cadherin, Her2/neu, Estrogen receptor, p53, progesterone receptor, beta catenin; donkey anti-mouse (Jackson Immunoresearch, 715-166-150); or donkey anti rabbit (Jackson Immunoresearch, 711-166-152).

In some embodiments, a binder may be sequence-specific. A sequence-specific binder may include a nucleic acid and the binder may be capable of recognizing a particular linear arrangement of nucleotides or derivatives thereof in the target. In some embodiments, the linear arrangement may include contiguous nucleotides or derivatives thereof that may each bind to a corresponding complementary nucleotide in the binder. In an alternate embodiment, the sequence may not be contiguous as there may be one, two, or more nucleotides that may not have corresponding complementary residues on the probe. Suitable examples of nucleic acid-based binders may include, but are not limited to, DNA or RNA oligonucleotides or polynucleotides. In some embodiments, suitable nucleic acids may include nucleic acid analogs, such as dioxygenin dCTP, biotin dcTP 7-aza-guanosine, azidothymidine, inosine, or uridine.

In certain embodiments, both the binder and the target may include nucleic acids. In some embodiments, a nucleic-acid based binder may form a Watson-Crick bond with the nucleic acid target. In another embodiment, the nucleic acid binder may form a Hoogsteen bond with the nucleic acid target, thereby forming a triplex. A nucleic acid binder that binds by Hoogsteen binding may enter the major groove of a nucleic acid target and hybridizes with the bases located there. Suitable examples of the above binders may include molecules that recognize and bind to the minor and major grooves of nucleic acids (for example, some forms of antibiotics.) In certain embodiments, the nucleic acid binders may form both Watson-Crick and Hoogsteen bonds with the nucleic acid target (for example, bis PNA probes are capable of both Watson-Crick and Hoogsteen binding to a nucleic acid).

The length of nucleic acid binder may also determine the specificity of binding. The energetic cost of a single mismatch between the binder and the nucleic acid target may be relatively higher for shorter sequences than for longer ones. In some embodiments, hybridization of smaller nucleic acid binders may be more specific than the hybridization of longer nucleic acid probes, as the longer probes may be more amenable to mismatches and may continue to bind to the nucleic acid depending on the conditions. In certain embodiments, shorter binders may exhibit lower binding stability at a given temperature and salt concentration. Binders that may exhibit greater stability to bind short sequences may be employed in this case (for examples, bis PNA). In some embodiments, the nucleic acid binder may have a length in range of from about 4 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, from about 250 nucleotides to about 500 nucleotides, or from about 500 nucleotides to about 1000 nucleotides. In some embodiments, the nucleic acid binder may have a length in a range that is greater than about 1000 nucleotides. Notwithstanding the length of the nucleic acid binder, all the nucleotide residues of the binder may not hybridize to complementary nucleotides in the nucleic acid target. For example, the binder may include 50 nucleotide residues in length, and only 25 of those nucleotide residues may hybridize to the nucleic acid target. In some embodiments, the nucleotide residues that may hybridize may be contiguous with each other. The nucleic acid binders may be single stranded or may include a secondary structure. In some embodiments, a biological sample may include a cell or a tissue sample and the biological sample may be subjected to in-situ hybridization (ISH) using a nucleic acid binder. In some embodiments, a tissue sample may be subjected to in situ hybridization in addition to immunohistochemistry (IHC) to obtain desired information from the sample.

Regardless of the type of binder and the target, the specificity of binding between the binder and the target may also be affected depending on the binding conditions (for example, hybridization conditions in case of complementary nucleic acids). Suitable binding conditions may be realized by modulation one or more of pH, temperature, or salt concentration.

A binder may be intrinsically labeled (signal generator or enzyme attached during synthesis of binder) or extrinsically labeled (signal generator or enzyme attached during a later step). For example for a protein-based binder, an intrinsically labeled binder may be prepared by employing labeled amino acids. Similarly, an intrinsically labeled nucleic acid may be synthesized using methods that incorporate signal generator-labeled nucleotides or signal generator labeled nucleoside phosphoramidites directly into the growing nucleic acid depending upon the method used for nucleic acid synthesis. In some embodiments, a binder may be synthesized in a manner such that signal generators or enzymes may be incorporated at a later stage. For example, this latter labeling may be accomplished by chemical means by the introduction of active amino or thiol groups into nucleic acids or peptide chains. In some embodiments, a binder such as a protein (for example, an antibody) or a nucleic acid (for example, a DNA) may be directly chemically labeled using appropriate chemistries.

In some embodiments, combinations of binders may be used that may provide greater specificity or in certain embodiments amplification of the signal. Thus, in some embodiments, a sandwich of binders may be used, where the first binder may bind to the target and serve to provide for secondary binding, where the secondary binder may or may not include a label, which may further provide for tertiary binding (if required) where the tertiary binding member may include a label.

Suitable examples of binder combinations may include primary antibody-secondary antibody, complementary nucleic acids, or other ligand-receptor pairs (such as biotin-streptavidin). Some specific examples of suitable binder pairs may include mouse anti-myc for recombinant expressed proteins with c-myc epitope; mouse anti-HisG for recombinant protein with His-Tag epitope, mouse anti-express for recombinant protein with epitope-tag, rabbit anti-goat for goat IgG primary molecules, complementary nucleic acid sequence for a nucleic acid; mouse anti-thio for thioredoxin fusion proteins, rabbit anti-GFP for fusion protein, jacalin for alpha.-D-galactose; and melibiose for carbohydrate-binding proteins, sugars, nickel couple matrix or heparin.

In some embodiments, a combination of a primary antibody and a secondary antibody may be used as a binder. A primary antibody may be capable of binding to a specific region of the target and the secondary antibody may be capable of binding to the primary antibody. A secondary antibody may be attached to a signal generator or an enzyme before binding to the primary antibody or may be capable of binding to a signal generator or an enzyme at a later step. In an alternate embodiment, a primary antibody and specific binding ligand-receptor pairs (such as biotin-streptavidin) may be used. The primary antibody may be attached to one member of the pair (for example biotin) and the other member (for example streptavidin) may be labeled with a signal generator or an enzyme. The secondary antibody, avidin, streptavidin, or biotin may be each independently labeled with a signal generator or an enzyme.

In some embodiments, the methods disclosed herein may be employed in an immunostaining procedure, and a primary antibody may be used to specifically bind the target protein. A secondary antibody may be used to specifically bind to the primary antibody, thereby forming a bridge between the primary antibody and a subsequent reagent (for example a signal generator or enzyme), if any. For example, a primary antibody may be mouse IgG (an antibody created in mouse) and the corresponding secondary antibody may be goat anti-mouse (antibody created in goat) having regions capable of binding to a region in mouse IgG.

In some embodiments, signal amplification may be obtained when several secondary antibodies may bind to epitopes on the primary antibody. In an immunostaining procedure a primary antibody may be the first antibody used in the procedure and the secondary antibody may be the second antibody used in the procedure. In other embodiments a third antibody may be used to further increase signal. For example, an antibody raised in mouse may be used to bind the target. A goat-anti-mouse secondary antibody may be used to bind the primary antibody and a labeled donkey-anti-goat antibody may be used as a tertiary antibody to bind to the secondary antibodies already bound to the primary antibody which itself is bound to the target. In some embodiments, a primary antibody may be the only antibody used in an immunostaining procedure.

Signal Generators

The type of signal generator suitable for the methods disclosed herein may depend on a variety of factors, including the nature of the analysis being conducted, the type of the energy source and detector used, the type of electron-transfer photoinitiating reagent employed, the type of binder, or the type of target.

A suitable signal generator may include a molecule or a compound capable of providing a detectable signal. A signal generator may provide a characteristic signal following interaction with an energy source or a current. An energy source may include electromagnetic radiation source and a fluorescence excitation source. Electromagnetic radiation source may be capable of providing electromagnetic energy of any wavelength including visible, infrared and ultraviolet. Electromagnetic radiation may be in the form of a direct light source or may be emitted by a light emissive compound such as a donor fluorophore. A fluorescence excitation source may be capable of making a source fluoresce or may give rise to photonic emissions (that is, electromagnetic radiation, directed electric field, temperature, physical contact, or mechanical disruption). Suitable signal generators may provide a signal capable of being detected by a variety of methods including optical measurements (for example, fluorescence), electrical conductivity, or radioactivity. Suitable signal generators may be, for example, light emitting, energy accepting, fluorescing, radioactive, or quenching.

A suitable signal generator may be sterically and chemically compatible with the constituents to which it is bound, for example, a binder. Additionally, a suitable signal generator may not interfere with the binding of the binder to the target, nor may it significantly affect the binding specificity of the binder. A suitable signal generator may be organic or inorganic in nature. In some embodiments, a signal generator may be of a chemical, peptide or nucleic acid nature.

A suitable signal generator may be directly detectable. A directly detectable moiety may be one that may be detected directly by its ability to emit a signal, such as for example a fluorescent label that emits light of a particular wavelength following excitation by light of another lower, characteristic wavelength and/or absorb light of a particular wavelength.

A signal generator, suitable in accordance with the methods disclosed herein may be amenable to manipulation on application of an electron-transfer photoinitiating reagent. In some embodiments, a signal generator may be capable of being bleached, e.g., the signal it generates may be diminished or destroyed as result of the signal generator being modified in the course of a photoreaction. Chemical modification may include complete disintegration of the signal generator or modification of the signal-generating component of the signal generator. In some embodiments, the signal generator is charged.

Modification of the signal-generating component may include any chemical modification (such as addition, substitution, or removal) that may result in the modification of the signal generating properties. For example, unconjugating a conjugated signal generator may result in destruction of chromogenic properties of the signal generator. Similarly, substitution of a fluorescence-inhibiting functional group on a fluorescent signal generator may result in modification of its fluorescent properties. In some embodiments, one or more signal generators substantially resistant to inactivation by a specific chemical agent may be used as a control probe in the provided methods.

In some embodiments, a signal generator may be selected from a light emissive molecule, a radioisotope (e.g., $P^{32}$ or $H^3$, $^{14}C$, $^{125}I$ and $^{131}I$), an optical or electron density marker, a Raman-active tag, an electron spin resonance molecule (such as for example nitroxyl radicals), an electrical charge transferring molecule (i.e., an electrical charge transducing molecule), a semiconductor nanocrystal, a semiconductor nanoparticle, a colloid gold nanocrystal, a microbead, a magnetic bead, a paramagnetic particle. The signal generators may or may not interact with the electron transfer reagent and may or may not be modified under some or all conditions used for modifying other signals.

In some embodiments, a signal generator may be an optical signal generator, e.g., may include a light-emissive molecule. A light emissive molecule may emit light in response to irradiation with light of a particular wavelength. Light emissive molecules may be capable of absorbing and emitting light through luminescence (non-thermal emission of electromagnetic radiation by a material upon excitation), phosphorescence (delayed luminescence as a result of the absorption of radiation), chemiluminescence (luminescence due to a chemical reaction), fluorescence, or polarized fluorescence. Non-limiting examples of optical signal generators include a fluorescent signal generator, e.g., a fluorophore, a Raman-active tag or a chromophore.

In some embodiments, a signal generator may essentially include a fluorophore. In some embodiments, a signal generator may essentially include a fluorophore attached to an antibody, for example, in an immunohistochemistry analysis. Suitable fluorophores that may be conjugated to a primary antibody include, but are not limited to, Fluorescein, Rhodamine, Texas Red, VECTOR Red, ELF (Enzyme-Labeled Fluorescence), Cy2, Cy3, Cy3.5, Cy5, Cy7, Fluor X, Calcein, Calcein-AM, CRYPTOFLUOR, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY, boron dipyrromethene difluoride, 1,3-dichloro-7-hydroxy-9,9-dimethyl-2(9H)-Acridinone (DDAO), dimethylacridinone (DAO), Oregon Green, MITOTRACKER Red, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, Infra-Red (IR) Dyes, Cyclic GDP-Ribose (cGDPR), Calcofluor White, Lissamine, Umbelliferone, Tyrosine or Tryptophan. In some embodiments, the fluorophore can be cyanine, rhodamine, coumarins or pyrelium dyes. In some embodiments, a signal generator may essentially include a cyanine dye. In further embodiments, a signal generator may essentially include one or more a Cy2 dye, a Cy3 dye, a Cy5 dye, or a Cy7 dye. In alternative embodiments, the signal generator may be BODIPY, rhodamine, 1,3-dichloro-7-hydroxy-9,9-dimethyl-2(9H)-Acridinone (DDAO) or 7-hydroxy-9,9-dimethyl-2(9H)-Acridinone (DAO).

In some embodiments, the signal generator may be part of a FRET pair. FRET pair includes two fluorophores that are capable of undergoing FRET to produce or eliminate a detectable signal when positioned in proximity to one another. Some examples of donors may include Alexa 488, Alexa 546, BODIPY 493, Oyster 556, Fluor (FAM), Cy3, or TTR (Tamra). Some examples of acceptors may include Cy5, Alexa 594, Alexa 647, or Oyster 656.

As described hereinabove, one or more of the aforementioned molecules may be used as a signal generator. In some embodiments, one or more of the signal generators may be amenable to signal destruction and the signal generator may essentially include a molecule capable of being bleached by photoactivated chemical bleaching. In some embodiments, a signal generator may include a fluorophore capable of being chemically modified in a photoreaction that also involves an electron-transfer photoinitiating reagent and irradiation. In some embodiments, a signal generator may essentially include cyanine, BODIPY, rhodamine, or acridinone (e.g., DDAO and DAO), that can be modified in a photoreaction that also involves addition of an electron-transfer photoinitiating reagent and irradiation. In some embodiments, a signal generator may include one or more a Cy2 dye, a Cy3 dye, a Cy5 dye, or a Cy7 dye that can be bleached by photoactivated chemical bleaching.

Enzyme and Enzyme Substrates

In some embodiments, a probe may include a binder coupled to an enzyme. In some embodiments, a suitable enzyme catalyzes a chemical reaction of the substrate to form a reaction product that can bind to a receptor (e.g., phenolic groups) present in the sample. A receptor may be exogeneous (that is, a receptor extrinsically adhered to the sample or the solid-support) or endogeneous (receptors present intrinsically in the sample or the solid-support). Signal amplification may be effected as a single enzyme may catalyze a chemical reaction of the substrate to covalently bind multiple signal generators near the target.

In some embodiments, a suitable enzyme may also be capable of being inactivated in the course of a photoreaction. Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase. In some embodiments, the enzyme is a peroxidase selected from horseradish peroxidase, cytochrome C peroxidase, glutathione peroxidase, microperoxidase, myeloperoxidase, lactoperoxidase, and soybean peroxidase.

In some embodiments, an enzyme is not inactivated in the course of a photoreaction, but is inactivated in a separate inactivation step carried out before or after the photoreaction is completed. The inactivation step may include application of an enzyme inactivation reagent to the sample containing the enzyme.

In some embodiments, a binder and an enzyme may be embodied in a single entity, for example a protein molecule capable of binding to a target and also catalyzing a chemical reaction of substrate. In other embodiments, a binder and an enzyme may be embodied in separate entities and may be coupled by covalent bond formation or by using ligand-receptor conjugate pairs (e.g., biotin streptavidin).

An enzyme substrate may be selected depending on the enzyme employed and the target available for binding in the sample. For example, in embodiments including HRP as an enzyme, a substrate may include a substituted phenol (e.g., tyramine or tyramide). Reaction of HRP to the tyramine may produce an activated phenolic substrate that may bind to endogeneous receptors like electron-rich moieties (such as tyrosine or tryptophan) or phenolic groups present in the surface proteins of a biological sample. In alternate embodiments, where 3-methyl-2-benzothiazolinone hydrochloride (MBTH) may be employed as a substrate along with an HRP enzyme, exogeneous receptors like p-dimethylaminobenzaldehyde (DMAB) may be adhered to the solid support or the biological sample before reacting with the substrate.

In some embodiments, an enzyme substrate may be dephosphorylated after reaction with the enzyme. The dephosphorylated reaction product may be capable of binding to endogeneous or exogeneous receptors (e.g., antibodies) in the sample or the solid-support. For example, an enzyme may include alkaline phosphatase (AP) and a substrate may include NADP or substituted phosphates (e.g., nitrophenyl phosphate). The receptors may include NAD binding proteins, antibodies to the dephosphorylated reaction product (e.g., anti-nitro-phenol), avidin, or streptavidin accordingly. In some embodiments, a substrate may produce insoluble product upon action of the enzyme which may deposit in vicinity of where they are generated. Non-limiting examples of such substrates may include diaminobenzidine (DAB) for HRP and ELF for AP.

In some embodiments, an enzyme may include β-galactosidase and a substrate may include β-galactopyranosyl-glycoside of fluorescein or coumarin. Receptors may include antibodies to deglycosylated moieties (e.g., anti-fluorescein or anti-coumarin). In some embodiments, multiple enzyme combinations like HRP/AP may be used as an enzyme. A substrate may include phosphorylated substituted phenol e.g., tyrosine phosphate, which may be dephosphorylated by AP before reacting with HRP to form a reaction product capable of binding to phenolic groups or electron rich moieties-based receptors.

A reaction product of the enzyme substrate may further be capable of providing a detectable signal. In some embodiments, enzyme substrates employed in the methods disclosed herein may include non-chromogenic or non-chemiluminescent substrates, that is a reaction of the enzyme and the enzyme substrate may not itself produce a detectable signal. Enzyme substrates employed in the methods disclosed herein may include an extrinsic signal generator (e.g., a fluorophore) as a label. The signal generator and the enzyme substrate may be attached directly (e.g., an enzyme substrate with a fluorescent label) or indirectly (e.g., through ligand-receptor conjugate pair). In some embodiments, a substrate may include protected functional groups (e.g., sulfhydryl groups). After binding of the activated substrate to the receptors, the functional group may be deprotected and conjugation to a signal generator effected using a signal generator having a thiol reactive group (e.g., maleimide or iodoacetyl).

In some embodiments, a probe may include horseradish peroxidase and the substrate is selected from substituted phenols (e.g., tyramine). In some embodiments, the horseradish peroxidase causes the activated phenolic substrate to covalently bind to the sample. In some embodiments, a probe may include a binder coupled to HRP and a substrate may include tyramine-coupled to a fluorophore.

Electron-Transfer Photoinitiating Reagents and Photoreaction

In certain embodiments the reagent used in the photoreaction, to substantially inactivates the signal generator) may be an electron-transfer photoinitiating reagent. An electron-transfer photoinitiating reagent may include one or more chemicals that can engage in a photoreaction with a molecule capable of undergoing photoexcitation. The molecule capable of undergoing photoexcitation may be a signal generator. An electron-transfer photoinitiating reagent may be contacted with the sample in the form of a solid, a solution, a gel, or a suspension.

In certain embodiments, an electron-transfer photoinitiating reagent may include a borate compound having a net positive charge with an anionic counter ion, or a zwitterionic borate having a net neutral charge. Fundamentally, the process works by shining light (broad spectrum or at or near wavelength suitable for dye excitation) onto a fluorescent dye labeled substrate in the presence of an electron transfer based photo initiator reagent. The photons excite the dye molecule (biomarker) and an electron transfer from borate to the dye molecule takes place. The subsequent degradation of the intermediate boranyl radical results in an alkyl radical formation that reacts with the dye to cause its bleaching.

The borate compound is represented by Formula I:

$$R_1R_2R_3R_4BX_a \qquad I$$

where each $R_1$, $R_2$, and $R_3$ and $R_4$ is, independently, an alkyl, an alkylaryl, an arylalkyl, or an aryl, with the proviso that at least one of $R_1$, $R_2$, and $R_3$ and $R_4$ is an alkyl group and at least one of $R_1$, $R_2$, and $R_3$ and $R_4$ group is positively charged; and X is an anion;

a equals 0, 1, 2, or 3.

In preferred embodiments Formula I is such that a equals 1, 2, or 3. The increase charge may provide improved stability and/or solubility which is important to allow for the desired reaction to occur.

In some embodiments, at least one R group ($R_1$, $R_2$, and $R_3$ and $R_4$) is positively charged and the R group may be an aryl, linear alkyl, cyclic alkyl, heteroalkyl, trialkylaniline, N-alkyl pyridine, N-alkyl alkyl ammonium. For example at least one R group may be 2-(trimethylamino)ethyl. In some embodiments the R group may be 4-(trimethylamino)phenyl. In some embodiments, X is a counter ion such as, but not limited to, a halide, sulfonate, acetate, nitrate, phosphate esters, or a carboxylate.

Examples of the borate compound represented by Formula I where a equals 0, such that the borate is an internal salt and therefore neutral, include the following structures:

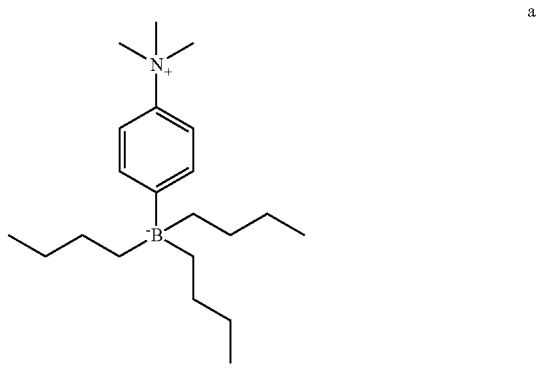

a

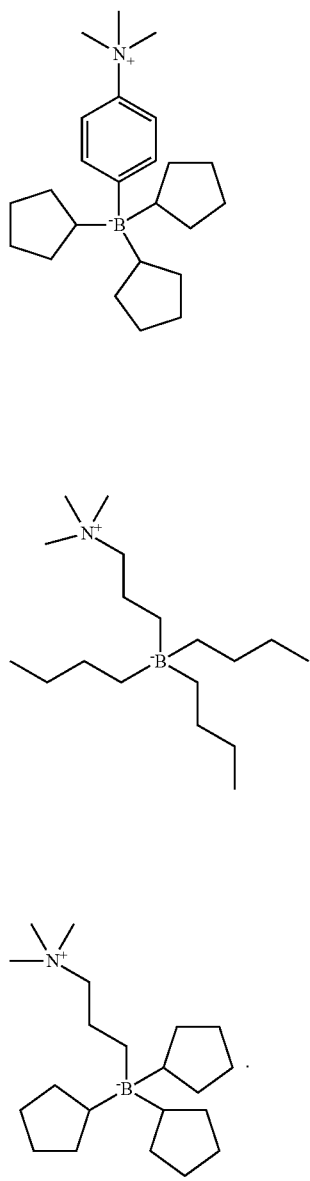
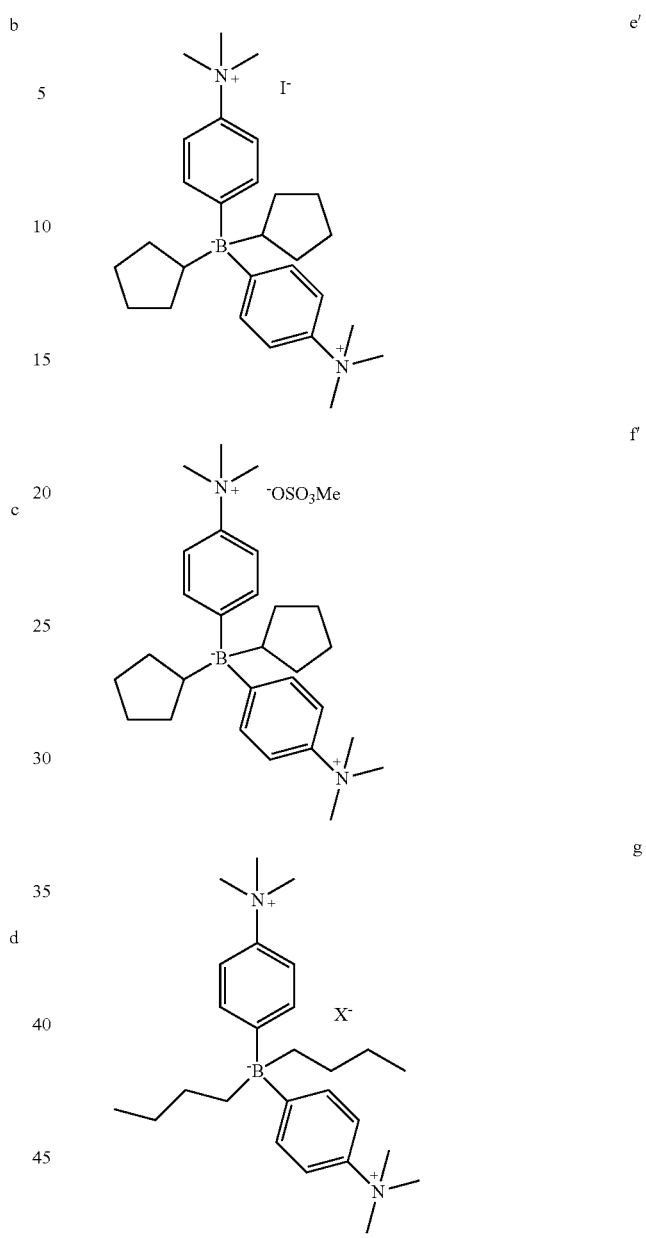
Examples of the borate compound represented by Formula I where a equals 1 such that the borate has a counter ion, include:
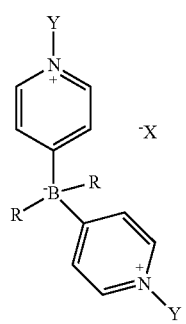
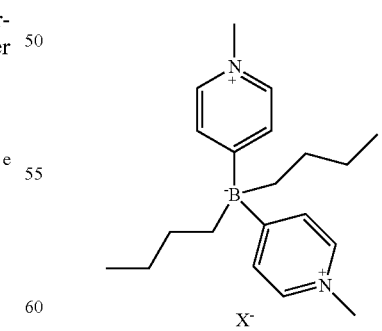
where Y is an alkyl group, alkylaryl, arylalkyl, or an aryl and X is a counter ion such as, but not limited to, a halide, sulfonate, acetate, nitrate, phosphate esters, or a carboxylate. These borates may offer the advantage of greater stability and/or reactivity compared to neutral borates. Reactivity may also be influenced by the relative solubility of the borate and the solvents selective.

Examples of the borate compound represented by Formula I, where a equals 2 or 3, such that the borate has more than one counter ion includes:

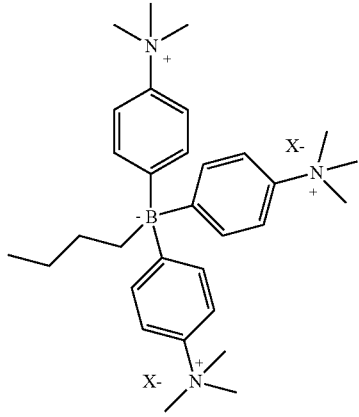

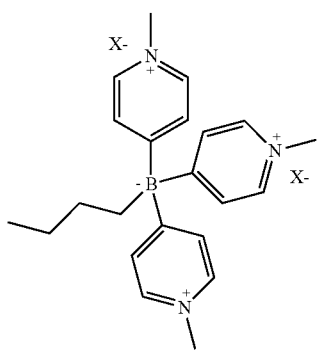

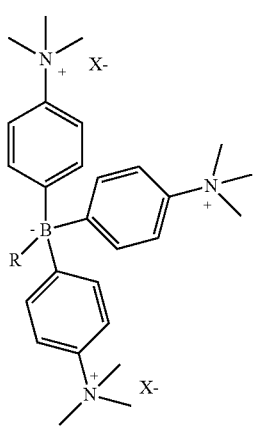

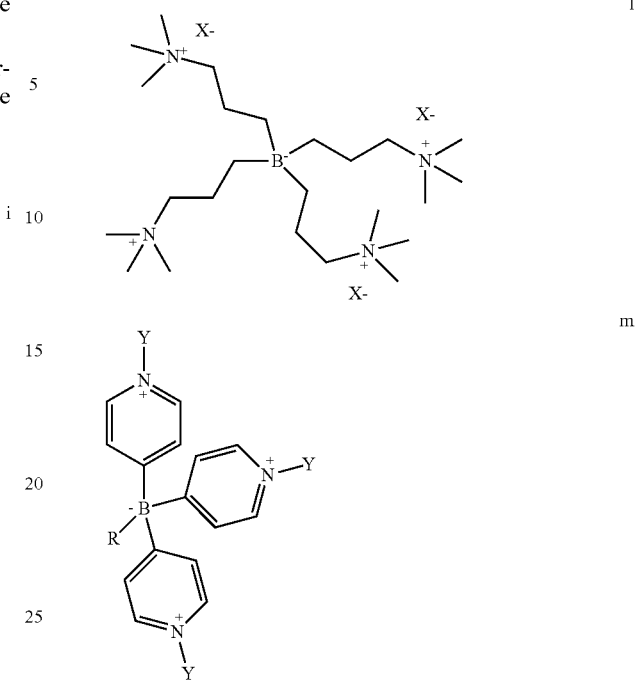

where R is an alkyl group, and X is a counter ion such as, but not limited to, a halide, sulfonate, acetate, nitrate, phosphate esters, or a carboxylate.

Preferably, an electron-transfer photoinitiating reagent to be used for photoactivated chemical bleaching is chosen such that the photoreaction between the electron-transfer photoinitiating reagent and a signal generator is energetically favorable. In some embodiments, the electron-transfer photoinitiating reagent and the photoexcited signal generator form an electron donor/acceptor pair, wherein an electron transfer from the electron-transfer photoinitiating reagent to the signal generator is energetically favorable. The electron transfer may further lead to chemical modification of the signal generator, resulting in bleaching of the signal generator. Examples of electron-transfer photoinitiating reagents and signal generators that can form electron donor/acceptor pairs include the borates as described above as an electron-transfer photoinitiating reagent and xanthene dyes, such as eosin, fluorescein, erythrosine, cyanine dyes, such as Cy3, Cy5, Cy7, etc. or acridinone dyes (DDAO, DAO) as signal μgenerators.

One or more of the aforementioned electron-transfer photoinitiating reagents may be used in the methods disclosed herein depending upon susceptibility of the signal generator, of the enzyme, of the binder, of the target, or of the biological sample to photoexcitation and/or subsequent photoreaction with the electron-transfer photoinitiating reagent. In some embodiments, photoexcitation of the signal generator by irradiation and subsequent photoreaction between the electron-transfer photoinitiating reagent and the photoexcited signal generator essentially does not affect the integrity of the binder, the target, and the biological sample. In some embodiments, photoexcitation of the signal generator by irradiation and subsequent photoreaction does not affect the specificity of binding between the binder and the target.

In some embodiments, the borate compound for use as a PICB agent may be in the form of a solution. In one embodiment, the borate compound is present in the form of a buffered aqueous solution. In more preferred embodiments, Formula I is such that a equals 1, 2, or 3 which may improve stability and/or solubility. In further embodiments, the borate compound may be present at a concentration of 0.001 uM to 1000 uM. In a preferred embodiment, the concentration of the borate compound is from 20 uM to 100 uM. In certain embodiments, the borate compound may be present at a concentration of 0.001 uM to 10 uM and more preferably at a concentration of 200 uM to 10 uM.

Irradiation of the sample contacted with the borate compound may be carried out for a predetermined amount of time. The duration of irradiation may depend on the desired duration of the photoreaction between the borate compound and the optical stain. In some embodiments, the irradiation step may be performed for about 20 seconds to about 60 minutes, preferably for about 20 seconds to about 15 minutes, and even more preferably, for about 20 seconds to about 5 minutes. In some embodiments, the irradiation step may be performed until no residual signal is observed from the signal generator. In some embodiments, the irradiation step may be performed at room temperature.

In some embodiments, the photoreaction is carried out at a temperature of 4-50° C., more preferably, at a temperature of 20-30° C.

In some embodiments, the photoreaction is carried out in a solution. In some embodiments, the solution is a buffered solution. In a further embodiment, the buffered solution is the solution buffered in phosphate buffered saline (PBS). In some embodiments, the solution is buffered at pH of 5-9. In some embodiments the solution is in pure deionized water. In a preferred embodiment, the pH of the solution is 6-8.

In some embodiments, the photoreaction is carried out after incubation of the labeled sample in the borate solution, followed by washing of excess borate prior to irradiating the sample.

In some embodiments, a characteristic of the optical signal may be observed after the photoreaction to determine the effectiveness of the bleaching. For example, a color may be observed before the photoreaction and the color may be absent after the photoreaction. In some embodiments, a decrease in signal intensity by a predetermined amount may be referred to as signal modification, or photoactivated chemical bleaching, or bleaching. In some embodiments, modification of the signal or photoactivated chemical bleaching, may refer to a decrease in the signal intensity by an amount in a range of greater than about 50 percent. In some embodiments, modification of the signal or photoactivated chemical bleaching, may refer to a decrease in the signal intensity by an amount in a range of greater than about 60 percent. In some embodiments, modification of the signal or photoactivated chemical bleaching, may refer to a decrease in the signal intensity by an amount in a range of greater than about 80 percent. In some embodiments, modification of the signal or photoactivated chemical bleaching, may refer to a decrease in the signal intensity by an amount in a range of greater than about 90 percent. In some embodiments, modification of the signal or photoactivated chemical bleaching, may refer to a decrease in the signal intensity by an amount in a range of greater than about 95 percent. In some embodiments, modification of the signal, or photoactivated chemical bleaching, may refer to a decrease in the signal intensity by an amount in a range of about 100 percent, or to complete bleaching.

Figure 2:
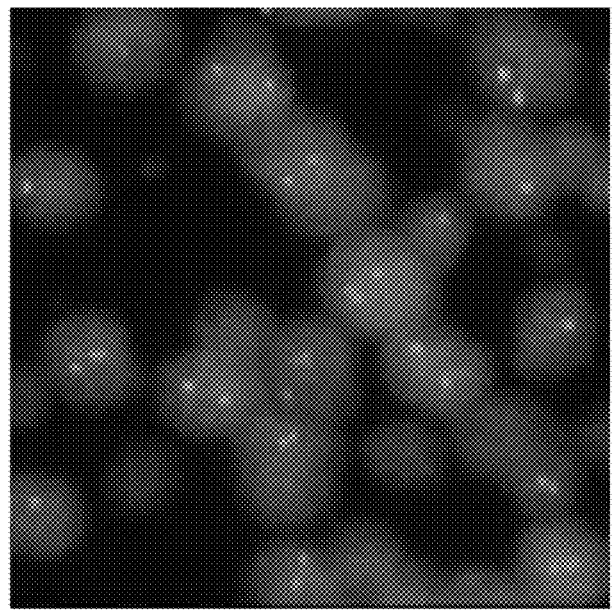
FIG. 2 are micrographs showing DNA FISH signal erased with the same borate (f'); (a) is the Her2 FISH signal and (b) is after bleaching.
Figure 2:
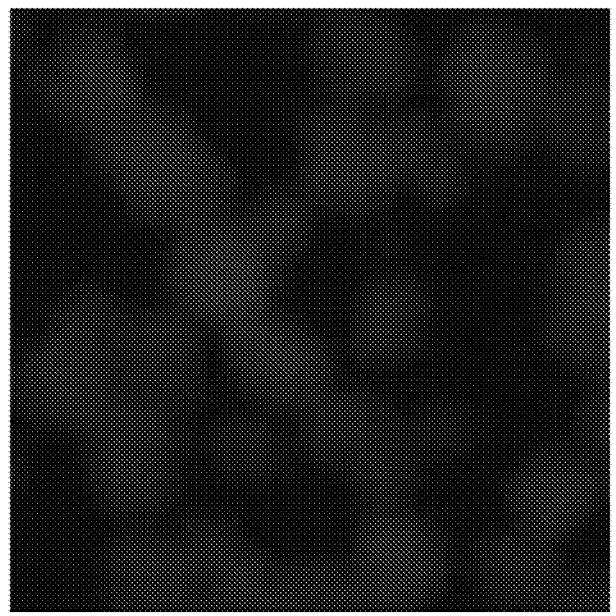

Results of photobleaching by representative borate compounds are shown graphically below in the Experimental section. FIG. 1 are micrographs showing efficient bleaching of eosin tissue using the cationic borate f' (Formula I) in the photactivated chemical bleaching. This is shown by viewing a tissue having residual eosin staining in the Cy3 channel (a) and in the Cy3 channel after bleaching with the borate f'(b) and after staining with PCK26 in the same channel (c). The corresponding non-H&E staining controls are shown in micrographs (d) and (e) respectively. FIG. 2 are micrographs showing DNA FISH signal erased with the same borate (f'). Micrograph (a) is the Her2 FISH signal and (b) is after bleaching.

In some embodiments, where two or more (up to 10 or thereabout) signal generators may be employed simultaneously, a photoreaction may be capable of selectively modifying one or more signal generators. This selectivity may be derived from selective photoexcitation of the signal generator by irradiation at specific wavelength. The irradiation wavelength is chosen such that one or more signal generator may be photoexcited, while the remaining one or more signal generator that may be present in a sample may remain unaffected. In some embodiments, irradiation limited to a range of wavelengths between 520-580 nm can be used for selective photoexciation of a Cy3 dye. In other embodiments, irradiation limited to a range of wavelengths between 620-680 nm can be used for selective photoexcitation of a Cy5 dye. In preferred embodiments, selective photoexcitation is accomplished by using a laser.

The propensity of photoexcited signal generators to further undergo photoreaction may depend on the choice of the electron-transfer photoinitiating reagent, as discussed above, as well as on the reaction conditions, such as temperature, solvent and pH.

In some embodiments, the photoactivated chemical bleaching is carried out at a temperature of 4-50° C., more preferably, at a temperature of 20-30° C.

In some embodiments, the photoactivated chemical bleaching is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

Sequentially Analyzing a Biological Sample, Contacting and Binding the Probe

A biological sample may be contacted with a probe to bind the probe to a target in the biological sample. In some embodiments, a target may not be easily accessible for binding with the probe and a biological sample may be further processed to facilitate the binding between the target and the binder in the probe, for example through antigen recovery, enzymatic digestion, epitope retrieval, or blocking.

In some embodiments, a probe may be contacted with the biological sample in the form of a solution. In some embodiments, a probe may include a binder coupled to a label (signal generator or an enzyme). The binder and the label (signal generator or enzyme) may be embodied in a single molecule and the probe solution may be applied in a single step. Alternatively, the binder and the label (signal generator or enzyme) may be distinct entities and the probe solution may be applied in a single step or multiple steps. In all embodiments, a control probe may further be bonded to one or more targets in the sample.

Depending on the nature of the binder, the target, and the binding between the two, sufficient contact time may be allowed. In some embodiments, an excess of probe molecules (and accordingly binder molecules) may be employed to ensure all the targets in the biological sample are bound.

After a sufficient time has been provided for the binding action, the sample may be contacted with a wash solution (for example, an appropriate buffer solution) to wash away any unbound probes. Depending on the concentration and type of probes used, a biological sample may be subjected to a number of washing steps with the same or different washing solutions being employed in each step.

In some embodiments, the biological sample may be contacted with more than one probe in the first binding step. The plurality of probes may be capable of binding different targets in the biological sample. For example, a biological sample may include two targets: target1 and target2 and two sets of probes may be used in this instance: probe1 (having binder1 capable of binding to target1) and probe2 (having binder2 capable of binding to target2). The plurality of probes may also comprise a plurality of multiple sets of target-binding probes. A plurality of probes may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

The number of probes that may be simultaneously bound to the target may depend on the type of detection employed, that is, the spectral resolution achievable. For example, for fluorescence-based signal generators, up to five different probes (providing up to five spectrally resolvable fluorescent signals) may be employed in accordance with the disclosed methods using standard microscopes. Spectrally resolvable, in reference to a plurality of fluorescent signal generators, indicates that the fluorescent emission bands of the signal generators are sufficiently distinct, that is, sufficiently non-overlapping, such that, binders to which the respective signal generators are attached may be distinguished on the basis of the fluorescent signal generated by the respective signal generators using standard photodetection systems. In other embodiments 8-10 probes may be employed simultaneous that are resolvable by more specialized microscope enabled with multispectral imaging and spectral deconvolution algorithms or fitted with specially designed narrow band filters. In some embodiments all probes may by simultaneously bound but the sequentially detected in sets of 1-10 probes per cycle.

In some embodiments, a biological sample may be essentially contacted with five or less than five probes in the first binding step. In embodiments employing enzyme-based probes, the number of probes that may be simultaneously bound to the target may also depend on the number of different enzymes and their corresponding substrates available.

In some embodiments, a biological sample may include a whole cell, a tissue sample, or the biological sample may be adhered to a microarray, a gel, or a membrane. In some embodiments, a biological sample may include a tissue sample. The tissue sample may be obtained by a variety of procedures including, but not limited to surgical excision, aspiration or biopsy. The tissue may be fresh or frozen. In some embodiments, the tissue sample may be fixed and embedded in paraffin. The tissue sample may be fixed or otherwise preserved by conventional methodology; the choice of a fixative may be determined by the purpose for which the tissue is to be histologically stained or otherwise analyzed. The length of fixation may depend upon the size of the tissue sample and the fixative used. For example, neutral buffered formalin, Bouin's or paraformaldehyde, may be used to fix or preserve a tissue sample.

In some embodiments, the tissue sample may be first fixed and then dehydrated through an ascending series of alcohols, infiltrated and embedded with paraffin or other sectioning media so that the tissue sample may be sectioned. In an alternative embodiment, a tissue sample may be sectioned and subsequently fixed. In some embodiments, the tissue sample may be embedded and processed in paraffin. Examples of paraffin that may be used include, but are not limited to, Paraplast, Broloid, and Tissuemay. Once the tissue sample is embedded, the sample may be sectioned by a microtome into sections that may have a thickness in a range of from about three microns to about five microns. Once sectioned, the sections may be attached to slides using adhesives. Examples of slide adhesives may include, but are not limited to, silane, gelatin, poly-L-lysine. In embodiments, if paraffin is used as the embedding material, the tissue sections may be deparaffinized and rehydrated in water. The tissue sections may be deparaffinized, for example, by using organic agents (such as, xylenes or gradually descending series of alcohols).

In some embodiments, aside from the sample preparation procedures discussed above, the tissue section may be subjected to further treatment prior to, during, or following immunohistochemistry. For example, in some embodiments, the tissue section may be subjected to epitope retrieval methods, such as, heating of the tissue sample in citrate buffer or Tris buffer or both in a sequential manner. In some embodiments, a tissue section may be optionally subjected to a blocking step to minimize any non-specific binding.

In some embodiments, the biological sample or a portion of the biological sample, or targets present in the biological sample may be adhered on the surface, e.g. DNA microarrays, or protein microarrays, or on the surface of solid supports (such as gels, blots, glass slides, beads, or ELISA plates). In some embodiments, targets present in the biological sample may be adhered on the surface of solid supports. Targets in the biological sample may be adhered on the solid support by physical bond formation, by covalent bond formation, or both.

In some embodiments, the targets in the biological sample may be adhered to membranes and probed sequentially using the methods disclosed herein. In some embodiments, targets in the biological sample may be processed before contacting the sample with the membrane. For example, embodiments involving methods for probing protein targets in a tissue sample may include the step of extracting the target proteins a biological sample of tissue homogenate or an extract. Solid tissues or whole cells may be first broken down mechanically using a blender (for larger sample volumes), using a homogenizer (smaller volumes), or by sonication. Different cell compartments and organelles may be separated using filtration and centrifugation techniques. Detergents, salts, and buffers may also be employed to encourage lysis of cells and to solubilize proteins. Similarly, embodiments involving methods for probing nucleic acids may include the step of preparing DNA or RNA fragments, for example using restriction endonucleases (for DNA).

In some embodiments, targets extracted from the biological sample may be further separated by gel electrophoresis. Separation of targets may be by isoelectric point (pI), molecular weight, electric charge, or a combination of these factors. The nature of the separation may depend on the treatment of the sample and the nature of the gel. A suitable gel may be selected from a polyacrylamide gel, an SDS-polyacrylamide gel, or an agarose gel.

A suitable membrane may be selected such that the membrane has non-specific target binding properties. In some embodiments, a suitable membrane may be selected from a polyvinylidene fluoride membrane, a nitrocellulose membrane, or a nylon membrane. In some embodiment, a suitable membrane may be selected such that the membrane may be substantially stable to multiple probing. In embodiments involving probing of targets using protein probes, the membranes may be blocked using a blocking solution to prevent non-specific binding of protein probes to the membranes. In embodiments, involving probing of DNA fragments, the DNA gel may be treated with a dilute HCL solution or an alkaline solution to facilitate more efficient transfer of the DNA from the gel to the membrane.

In some embodiments, the membrane may be subjected to temperatures in a range of about 60° C. to about 100° C. to covalently bind the targets to the membrane, for example DNA targets to a nitrocellulose membrane. In some embodiments, the membrane may be exposed to ultraviolet radiation to covalently bind the targets to the membrane, for example DNA targets to a nylon membrane. In some embodiments, the targets in the biological sample may not be separated by electrophoresis before blotting on a membrane and may be probed directly on a membrane, for example, in dot blot techniques.

Following the preparation of the tissue sample or the membrane, a probe solution (e.g., labeled-antibody solution) may be contacted with the tissue section or the membrane for a sufficient period of time and under conditions suitable for binding of binder to the target (e.g., antigen). As described earlier, two detection methods may be used: direct or indirect. In a direct detection, a signal generator-labeled primary antibody (e.g., fluorophore-labeled primary antibody or enzyme-labeled primary antibody) may be incubated with an antigen in the tissue sample or the membrane, which may be visualized without further antibody interaction. In an indirect detection, an unconjugated primary antibody may be incubated with an antigen and then a labeled secondary antibody may bind to the primary antibody. Signal amplification may occur as several secondary antibodies may react with different epitopes on the primary antibody. In some embodiments two or more (at most five) primary antibodies (from different species, labeled or unlabeled) may be contacted with the tissue sample. Unlabeled antibodies may be then contacted with the corresponding labeled secondary antibodies. In alternate embodiments, a primary antibody and specific binding ligand-receptor pairs (such as biotin-streptavidin) may be used. The primary antibody may be attached to one member of the pair (for example biotin) and the other member (for example streptavidin) may be labeled with a signal generator or an enzyme. The secondary antibody, avidin, streptavidin, or biotin may be each independently labeled with a signal generator or an enzyme.

In embodiments where the primary antibody or the secondary antibody may be conjugated to an enzymatic label, a fluorescent signal generator-coupled substrate may be added to provide visualization of the antigen. In some embodiments, the substrate and the fluorescent signal generator may be embodied in a single molecule and may be applied in a single step. In other embodiments, the substrate and the fluorescent signal generator may be distinct entities and may be applied in a single step or multiple steps.

An enzyme coupled to the binder may react with the substrate to catalyze a chemical reaction of the substrate to covalently bind the fluorescent signal generator-coupled substrate the biological sample. In some embodiments, an enzyme may include horseradish peroxidase and the substrate may include tyramine. Reaction of the horseradish peroxidase (HRP) with the tyramine substrate may cause the tyramine substrate to covalently bind to phenolic groups present in the sample. In embodiments employing enzyme-substrate conjugates, signal amplification may be attained as one enzyme may catalyze multiple substrate molecules. In some embodiments, methods disclosed herein may be employed to detect low abundance targets using indirect detection methods (e.g., using primary-secondary antibodies), using HRP-tyramide signal amplification methods, or combinations of both (e.g., indirect HRP-tyramide signal amplification methods). Incorporation of signal amplification techniques into the methods disclosed herein and correspondingly the type of signal amplification techniques incorporated might depend on the sensitivity required for a particular target and the number of steps involved in the protocol.

Observing a Signal from the Probe or from the First Set of the Plurality of Probes A signal from the signal generator may be detected using a detection system. The nature of the detection system used may depend upon the nature of the signal generators used. The detection system may include an, a charge coupled device (CCD) detection system a fluorescent detection system, an electrical detection system, a photographic film detection system, a chemiluminescent detection system, an enzyme detection system, an optical detection system, a near field detection system, or a total internal reflection (TIR) detection system.

One or more of the aforementioned techniques may be used to observe one or more characteristics of a signal from a signal generator (coupled with a binder or coupled with an enzyme substrate). In some embodiments, signal intensity, signal wavelength, signal location, signal frequency, or signal shift may be determined using one or more of the aforementioned techniques. In some embodiments, one or more aforementioned characteristics of the signal may be observed, measured, and recorded.

In some embodiments, the observed signal is a fluorescent signal, and a probe bound to a target in a biological sample may include a signal generator that is a fluorophore. In some embodiments, the fluorescent signal may be measured by determining fluorescence wavelength or fluorescent intensity using a fluorescence detection system. In some embodiments, a signal may be observed in situ, that is, a signal may be observed directly from the signal generator associated through the binder to the target in the biological sample. In some embodiments, a signal from the signal generator may be analyzed within the biological sample, obviating the need for separate array-based detection systems.

In some embodiments, observing a signal may include capturing an image of the biological sample. In some embodiments, a microscope connected to an imaging device may be used as a detection system, in accordance with the methods disclosed herein. In some embodiments, a signal generator (such as, fluorophore) may be excited and the signal (such as, fluorescence signal) obtained may be observed and recorded in the form of a digital signal (for example, a digitalized image). The same procedure may be repeated for different signal generators (if present) that are bound in the sample using the appropriate fluorescence filters.

In some embodiments, multiple different types of signals may be observed in the same sample. For example, one target may be detected with a fluorescent probe and a second target in the same sample may be detected with a chromogenic probe.

Applying an Electron-Transfer Photoinitiating Reagent and Irradiating to Initiate a Photoreaction to Modify the Signal To modify the signal, the borate compound of Formula I, which acts as an electron-transfer photoinitiating reagent, may be applied to the sample, and the sample may subsequently be irradiated to initiate a photoreaction. In some embodiments, signal modification may include a change in one or more signal characteristics, for example, a decrease in intensity of signal, a shift in the signal peak, or a change in the resonant frequency. In some embodiments, a photoreaction may modify the signal by substantially inactivating, i.e., bleaching, the fluorescent signal generator and the enzyme (if employed).

In some embodiments, the borate salt may be in the form of a solution. In one embodiment, the borate salt is present in the form of an aqueous solution. In one embodiment, the aqueous solution is a buffered aqueous solution. In further embodiments, the borate compound present at a concentration of 0.001 mM to 1000 mM. In a preferred embodiment, the concentration of triphenyl butyl borate is from 20 mM to 100 mM.

Irradiation of the sample contacted with the electron-transfer photoinitiating reagent may be carried out for a predetermined amount of time. The duration of irradiation may depend on the desired duration of the photoreaction between the electron-transfer photoinitiating reagent and the photoexcited signal generator. In some embodiments, the irradiation step may be performed for about 20 seconds to about 60 minutes, preferably for about 20 seconds to about 15 minutes, and even more preferably, for about 20 seconds to about 5 minutes. In some embodiments, the irradiation step may be performed until no residual signal is observed from the signal generator. In some embodiments, the irradiation step may be performed at room temperature.

In some embodiments, the photoreaction is carried out at a temperature of 4-50° C., more preferably, at a temperature of 20-30° C.

In some embodiments, excess electron-transfer photoinitiating agent may be removed by dipping or washing the sample in an aqueous buffer or water prior to irradiating the sample.

In some embodiments, the photoreaction is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

In some embodiments, the conditions for a photoreaction (e.g., irradiation wavelength) may be selected such that the binder, the target, the biological sample, and binding between the binder and the target may not be affected by the photoreaction. In some embodiments, the photoreaction may only affect the signal generator and the enzyme (if employed) and the electron-transfer photoinitiating reagent, and may not affect the target/binder binding or the binder integrity. Thus, by way of example, a binder may include a primary antibody or a primary antibody/secondary combination. A photoreaction according to the methods disclosed herein may only affect the signal generator, and the primary antibody or primary antibody/secondary antibody combination may essentially remain unaffected. In some embodiments, a binder (such as, a primary antibody or primary antibody/secondary antibody combination) may remain bound to the target in the biological sample after contacting the sample with the electron-transfer photoinitiating reagent and subsequent irradiation to initiate a photoreaction.

In some embodiments, a characteristic of the signal may be observed after the photoreaction to determine the effectiveness of the signal modification. For example, a color may be observed before the photoreaction and the color may be absent after the photoreaction. In another example, fluorescence intensity from a fluorescent signal generator may be observed before the photoreaction and after the photoreaction. In some embodiments, a decrease in signal intensity by a predetermined amount may be referred to as signal modification, or photoactivated chemical bleaching, or bleaching. In some embodiments, modification of the signal, or photoactivated chemical bleaching, may refer to a decrease in the signal intensity by an amount in a range of greater than about 50 percent. In some embodiments, modification of the signal, or photoactivated chemical bleaching, may refer to a decrease in the signal intensity by an amount in a range of greater than about 60 percent. In some embodiments, modification of the signal, or photoactivated chemical bleaching, may refer to a decrease in the signal intensity by an amount in a range of greater than about 80 percent. In some embodiments, modification of the signal, or photoactivated chemical bleaching, may refer to a decrease in the signal intensity by an amount in a range of greater than about 90 percent. In some embodiments, modification of the signal, or photoactivated chemical bleaching, may refer to a decrease in the signal intensity by an amount in a range of greater than about 95 percent. In some embodiments, modification of the signal, or photoactivated chemical bleaching, may refer to a decrease in the signal intensity by an amount in a range of about 100 percent, or to complete bleaching.

Contacting the Sample with a Subsequent Probe and Binding to a Subsequent Target The biological sample or the sample may be contacted with a subsequent probe using one or more procedures described herein above for the first probe. The subsequent probe may be capable of binding to target different from the target bound in the earlier steps. In embodiments where a plurality of probes may be contacted with the biological sample in the earlier probe contact steps, the subsequent probe may be capable of binding a target different from the targets bound by the earlier probe set. In some embodiments, a biological sample may be contacted with a plurality of probes in the subsequent probe contact step. In some embodiments, where a plurality of multiple sets of probes was applied to a biological sample in the first step, a subsequent set of signals from the subsequent set of probes may be generated. Generation of the second set of signals may comprise associating the second set of probes with a separate moiety that comprises signal generator. For example, the second set of probes may comprise a biotin tag, and the moiety comprising signal generator may also comprise streptavidin capable of binding the biotin tag. Alternatively, generation of the second set of signals may comprise un-masking the signal-generating moiety, e.g., by modifying the distance between the fluorophore-quencher pair. In some embodiments generation of the second set of signals may be by hybridization of labeled probes complementary to sequences attached to the second set of probes.

In embodiments where binders coupled to enzymes may be employed as probes, binding steps may further include reacting steps involving reaction of the enzyme with an enzyme substrate coupled to fluorescent signal generator.

In some embodiments, the signal generator (e.g., a fluorescent signal generator) used in the different binding steps may be the same, that is, detectable in the same detection channel. Methods employing the same signal generator in different binding steps may allow for detection of multiple targets when limited numbers of detection channels are available. In some embodiments, where a set of probes (2 to 5 probes) may be employed in the first binding step, the subsequent probes may include the same signal generators as in the earlier binding steps. For example, a first binding step may include Cy3, Cy5, and Cy7-conjugated different binders. In some embodiments, the subsequent binding steps may also include the same dye set, that is, Cy3, Cy5, and Cy7.

In some embodiments, the signal generator (e.g., a fluorescent signal generator) used in the different binding steps may be different, that is, independently detectable in different detection channels. For example, in some embodiments, a first probe may include a Cy3 dye, which has a fluorescent emission wavelength in the green region and a subsequent probe may include a Cy7 dye, which has a fluorescent emission wavelength in the near infrared region.

In embodiments employing binder-coupled enzymes as probes, the enzymes and the substrates employed in the different binding and reacting steps may be the same. An earlier enzyme may be inactivated in the course of a photoreaction or in a separate inactivation step before binding the sample to a subsequent enzyme to prevent cross-reaction of the earlier enzyme with the subsequent substrate. For example, a first binding and reacting step may include binder coupled to HRP and tyramine coupled to a first fluorophore. The photoinduced chemical bleaching (PICB) step may involve the steps of substantially inactivating the fluorophore and substantially inactivating the HRP. In some embodiments, photoinduced chemical bleaching and inactivation steps may occur simultaneously. In some embodiments, photoinduced chemical bleaching and inactivation steps may occur sequentially. After the photoinduced chemical bleaching and inactivation steps, the sample may be contacted with a subsequent binder coupled to HRP, which may be further reacted with tyramine coupled to a second fluorophore. Similarly, the subsequent binding and reacting steps may be affected using multiple iterations of HRP-tyramine as enzyme substrate conjugates, each binding and reacting step followed by the photoinduced chemical bleaching and inactivation step. The first fluorophore and the subsequent fluorophores may be the same or different depending on the number of detection channels available for detection.

In some embodiments, the first binding step may include a set of probes (e.g., 2 to 5 probes), each probe including a binder capable of binding to a different target and each enzyme capable of catalyzing a chemical reaction of a different substrate. For example, in one embodiment, the first probe set may include a binder1 coupled to HRP and a binder2 coupled to AP. The reacting step may include contacting the sample with tyramine-coupled to Cy3 and NADP-coupled to Cy7. Following reaction of the enzymes with their corresponding substrates and observing the signals, the cyanine dyes may be inactivated by photoinduced chemical bleaching and the enzymes inactivated in the course of a photoreaction or by addition of a suitable inactivating agent. The subsequent probing steps may include the same set of binder-enzyme and substrate-fluorophore pairs or different set of binder-enzyme and substrate-fluorophore pairs. The plurality of probes and the substrate-signal generator may be contacted with the biological sample simultaneously (for example, as a single mixture) or sequentially (for example, a probe1 may be contacted with the biological sample, followed by washing step to remove any unbound probe1, followed by contacting a probe2 with the biological sample, and so forth).

Observing a Subsequent Signal from a Subsequent Probe

One or more detection methods described hereinabove may be used to observe one or more characteristics of a subsequent (e.g., second, third, etc.) signal from a subsequent signal generator (present in the subsequent probe). In some embodiments, signal intensity, signal wavelength, signal location, signal frequency, or signal shift may be determined using one or more of the aforementioned techniques. Similar to the first signal, a subsequent signal (for example, a fluorescence signal) obtained may be recorded in the form of a digital signal (for example, a digitalized image). In some embodiments, observing a subsequent signal may also include capturing an optical image of the biological sample.

Reiteration of the Contacting, Binding, and Observing Steps

In some embodiments, after contacting the sample with a subsequent (e.g., second, third, etc.) probe, bleaching of the signal generator in a photoreaction, and subsequent probe administration signal generation from already bound probes may be repeated multiple times. In some embodiments, after observing a second signal from the second probe, the biological sample may be contacted with an electron-transfer photoinitiating reagent and irradiated to modify the signal from the second probe. Furthermore, a third probe may be contacted with the biological sample, wherein the third probe may be capable of binding a target different from the first and the second probes. Likewise, a signal from the third probe may be observed and followed by application of the borate compound or another electron-transfer photoinitiating reagent and irradiation to modify the signal. The binding, observing, and bleaching steps may be repeated iteratively multiple times using an $n^{th}$ probe capable of binding to additional targets to provide the user with information about a variety of targets using a variety of probes and/or signal generators. In embodiments where binders coupled to enzymes may be employed as probes, binding steps may further include reacting steps involving reaction of the enzyme with an enzyme substrate coupled to fluorescent signal generator.

In some embodiments, the bleaching, binding, reacting (if applicable), and observing steps may be repeated one or more time. In some embodiments, the bleaching, binding, reacting (if applicable), and observing steps may be repeated at least 5, at least 15, at least 30, at least 60 times, at least 100 times, or at least 150 times. In some embodiments, the series of steps may be repeated 25-30 times. In other embodiments, the series of steps may be repeated 2-10 times.

In some embodiments, a series of probes may be contacted with the biological sample in a sequential manner to obtain a multiplexed analysis of the biological sample. In some embodiments, a series of probe may be contacted with the biological sample in a sequential manner to obtain a multiplexed analysis of the biological sample. Multiplexed analysis generally refers to analysis of multiple targets in a biological sample using the same detection mechanism. In certain embodiments multispectral imaging, with sufficient resolution, may allow up to 10 or more probes in each probe set.

In some embodiments, where a biological sample is contacted with a plurality of multiple sets of probes in the first step, a series of steps comprising bleaching, generating signals from a subsequent set of probes and observing the signal may be repeated at least 5, at least 15, at least 30, at least 60 times, at least 100 times, or at least 150 times. In some embodiments, the series of steps may be repeated 25-30 times. In other embodiments, the series of steps may be repeated 2-10 times.

In some embodiments, the components of a biological sample are not significantly modified after repeated cycles the bleaching, binding, reacting (if applicable), and signal observing steps. In some embodiments, the components of a biological sample are not significantly modified during the bleaching step. In some embodiments, the components of the biological sample that are not significantly modified during the bleaching step are targets. In some embodiments, more than 80% of targets are not significantly modified in the course of the bleaching step. In some embodiments, more than 95% of targets are not significantly modified in the course of the bleaching step.

Contacting the Sample with One or More Morphological Stain

In some embodiments, a biological sample may include a cell or a tissue, and the sample may be contacted with a morphological stain before, during, or after the contacting step with the first probe or subsequent probe. A morphological stain may include a dye that may stain different cellular components, in order to facilitate identification of cell type or disease status. In some embodiments, the morphological stain may be readily distinguishable from the signal generators in the probes, that is, the stain may not emit signal that may overlap with signal from the probe. For example, for a fluorescent morphological stain, the signal from the morphological stain may not autofluoresce in the same wavelength as the fluorophores used in the probes.

A morphological stain may be contacted with the biological sample before, during, or after, any one of the aforementioned steps. In some embodiments, a morphological stain may be contacted with biological sample along with the first probe contact step. In some embodiments, a morphological stain may be contacted with the biological sample before contacting the sample with an electron-transfer photoinitiating reagent and irradiated after binding the first probe to the target. In some embodiments, a morphological stain may be contacted with a biological sample after contacting the sample with an electron-transfer photoinitiating reagent and irradiation to modify the signal. In some embodiments, a morphological stain may be contacted with a biological sample along with the second probe contact step. In some embodiments, a biological sample may be contacted with the morphological stain after binding the second probe to the target. In some embodiments, where the morphological stains may result in background noise for the fluorescent signal from the signal generator, the morphological stains may be contacted with the biological sample after the probing, bleaching and reprobing steps. For example, morphological stains like H&E may be sequentially imaged and registered after the methods disclosed herein.

As used herein the term "H&E stain" general refers to hematoxylin and eosin stain (H&E stain or HE stain). A histological section stained with H&E and is often termed "H&E section", "H+E section", or "HE section". The staining method involves application of hemalum, which is a complex formed from aluminum ions and oxidized haematoxylin. These colors nuclei of cells (and a few other objects, such as keratohyalin granules) blue. The nuclear staining is followed by counterstaining with an aqueous or alcoholic solution of eosin Y, which colors other, eosinophilic structures in various shades of red, pink and orange.

The staining of nuclei by hemalum does not require the presence of DNA and is probably due to binding of the dye-metal complex to arginine-rich basic nucleoproteins such as histones. The eosinophilic structures are generally composed of intracellular or extracellular protein. The Lewy bodies and Mallory bodies are examples of eosinophilic structures. Most of the cytoplasm is eosinophilic. Red blood cells are stained intensely red.

In some embodiments, chromophores, fluorophores, or enzyme/enzyme substrates may be used as morphological stains. Suitable examples of chromophores that may be used as morphological stains (and their target cells, subcellular compartments, or cellular components) may include, but are not limited to, Hematoxylin (nucleic acids), Orange G (red blood, pancreas, and pituitary cells), Light Green SF (collagen), Romanowsky-Giemsa (overall cell morphology), May-Grunwald (blood cells), Blue Counterstain (Trevigen), Ethyl Green (CAS) (amyloid), Feulgen-Naphthol Yellow S (DNA), Giemsa (differentially stains various cellular compartments), Methyl Green (amyloid), pyronin (nucleic acids), Naphthol-Yellow (red blood cells), Neutral Red (nuclei), Papanicolaou stain (a mixture of Hematoxylin, Orange G and Bismarck Brown mixture (overall cell morphology)), Red Counterstain B (Trevigen), Red Counterstain C (Trevigen), Sirius Red (amyloid), Feulgen reagent (pararosanilin) (DNA), Gallocyanin chrom-alum (DNA), Gallocyanin chrom-alum and Naphthol Yellow S (DNA), Methyl Green-Pyronin Y (DNA), Thionin-Feulgen reagent (DNA), Acridine Orange (DNA), Methylene Blue (RNA and DNA), Toluidine Blue (RNA and DNA), Alcian blue (carbohydrates), Ruthenium Red (carbohydrates), Sudan Black (lipids), Sudan IV (lipids), Oil Red-O (lipids), Van Gieson's trichrome stain (acid fuchsin and picric acid mixture) (muscle cells), Masson trichrome stain (hematoxylin, acid fuchsin, and Light Green mixture) (stains collagen, cytoplasm, nucleioli differently), Aldehyde Fuchsin (elastin fibers), or Weigert stain (differentiates reticular and collagenous fibers).

Examples of suitable fluorescent morphological stains (and their target cells, subcellular compartments, or cellular components if applicable) may include, but are not limited to: 4',6-diamidino-2-phenylindole (DAPI) (nucleic acids), Hoechst 33258 and Hoechst 33342 (two bisbenzimides) (nucleic acids), Propidium Iodide (nucleic acids), Spectrum Orange (nucleic acids), Spectrum Green (nucleic acids), Quinacrine (nucleic acids), Fluorescein-phalloidin (actin fibers), Chromomycin A 3 (nucleic acids), Acriflavine-Feulgen reaction (nucleic acid), Auramine O-Feulgen reaction (nucleic acids), Ethidium Bromide (nucleic acids). Nissl stains (neurons), high affinity DNA fluorophores such as POPO, BOBO, YOYO and TOTO and others, and Green Fluorescent Protein fused to DNA binding protein, such as histones, ACMA, Quinacrine and Acridine Orange.

Examples of suitable enzymes (and their primary cellular locations or activities) may include, but are not limited to, ATPases (muscle fibers), succinate dehydrogenases (mitochondria), cytochrome c oxidases (mitochondria), phosphorylases (mitochondria), phosphofructokinases (mitochondria), acetyl cholinesterases (nerve cells), lactases (small intestine), acid phosphatases (lysosomes), leucine aminopeptidases (liver cells), dehydrogenases (mitochondria), myodenylate deaminases (muscle cells), NADH diaphorases (erythrocytes), and sucrases (small intestine).

In some embodiments, a morphological stain may be stable towards photoactivated chemical bleaching, that is, the signal generating properties of the morphological stain may not be substantially affected by a photoreaction comprising contacting the morphological stain with an electron-transfer photoinitiating reagent and subsequent irradiation.

In some embodiments, where a biological sample may be stained with a probe and a morphological stain at the same time, a bleaching of the signal from the probe may not modify the signal from the morphological stain. In some embodiments, a morphological stain may be used as a control to co-register the molecular information (obtained through the iterative probing steps) and the morphological information (obtained through the morphological stains). In some embodiments, the morphological stain is not modified by the electron-transfer photoinitiating reagent upon irradiation of the sample.

In certain embodiments the methods may more specifically applied to detection of multiple targets in a single biological sample which is subjected to Hematoxylin and eosin stain (H&E) at some time during its analysis and allows for removal of the H&E signals from the tissue. The same tissue may then be subjected to immunofluorescence and FISH staining. In some embodiments, methods of detecting multiple targets in a single H&E stained biological sample using the same detection channel are disclosed. The invention includes embodiments that relate to methods applicable in analytical, diagnostic, or prognostic applications such as analyte detection, fluorescence-activated cell sorting (FACS), histochemistry, immunohistochemistry, or immunofluorescence. In some embodiments, the methods disclosed herein may be particularly applicable in histochemistry, immunostaining, immunohistochemistry, immunoassays, immunofluorescence or fluorescence in situ hybridization.

In some embodiments, the method disclosed comprises a two-step protocol wherein in the first step hematoxylin and a majority of the eosin is removed from the H&E stained sample by different washing protocols. In a second step, irreversible quenching of residual eosin fluorescence by photo-induced electron transfer based chemistry, herein referred to as Photoinduced Chemical Bleaching (PICB), and is then applied to remove the residual eosin signal. This PICB process involves excitation of eosin in the presence of an electron donor or acceptor. Following excitation an electron is transferred between the dye and either the donor or the acceptor and the resultant reactive dye undergoes further reaction or rearrangements with an accompanied change in optical properties. For example, a biological sample is stained with eosin. After imaging, the slide is flooded with a borate compound of Formula I in a buffer solution and light from mercury, halogen or xenon lamp, an LED or another light source is shined on the tissue to bleach the eosin signal. After signal bleaching, the biological sample is available for further molecular analysis either by IHC, IF or FISH.

While not definitive, the mechanism of eosin bleaching may be based on electron transfer from borate to the eosin molecule after the photoexcitation of the eosin followed by generation of an alkyl radical from borate radical degradation. Subsequent reaction of the dye with the alkyl radical or other species in the buffer may then destroy the dye signal. In some embodiments, the photoreaction comprises intermolecular electron transfer. In other embodiments, the photoreaction comprises intramolecular electron transfer.

In some embodiments, the eosin signal is irreversibly modified. In some embodiments, the eosin signal is irreversibly modified by a photoreaction that inactivates the signal generator by photoactivated chemical bleaching.

Contacting the Sample with One or More Control Probe

In some embodiments, a control probe may be bonded to one or more targets in the biological sample. In some embodiments, a control probe may be bonded to the targets along with the first probe contact step. In some embodiments, a control probe may be applied to the biological sample simultaneously with the first probe. In some embodiments, a control probe may be applied to the biological sample sequentially, that is before or after the application of the first probe, but before application of the electron-transfer photoinitiating reagent and subsequent irradiation.

A control probe may include a signal generator that is stable towards photoactivated chemical bleaching or the signal generating properties of the signal generator are not substantially affected when contacted with the electron-transfer photoinitiating reagent and subsequent irradiation. A signal generator may include a radioisotope that is stable during exposure to an electron-transfer photoinitiating reagent and irradiation or a fluorophore that is not chemically modified upon exposure to an electron-transfer photoinitiating reagent and irradiation. A suitable radioisotope may include $P^{32}$, $^3H$, $^{14}C$, $^{125}I$ or $^{131}I$. A suitable fluorophore may include DAPI.

In some embodiments, a suitable signal generator may be coupled to a binder to form a control probe. For example, a radioactive label may be coupled to an antibody to form a control probe and the antibody may bind to one or more target antigens present in the biological sample. In other embodiments, a suitable signal generator may be capable of binding to one more targets in the sample and also providing a detectable signal, which is stable in the presence of the electron-transfer photoinitiating reagent and during irradiation. For example, a suitable control probe may be DAPI, which is capable of binding to nucleic acids in the sample and also capable of providing a fluorescent signal that is substantially stable to photoactivated chemical bleaching, i.e., that is not substantially modified after addition of an electron-transfer photoinitiating reagent and subsequent irradiation at the selected wavelength range.

In some embodiments, a control probe may be employed in the methods disclosed herein to provide an indication of the stability of the targets to the iterative staining steps. For example, a control probe may be bonded to a known target in the sample and a signal from the control observed and quantified. The control signal may be then monitored during the iterative staining steps to provide an indication of the stability of the targets or binders to the electron-transfer photoinitiating reagent and subsequent irradiation. In some embodiments, a quantitative measure (for example, signal intensity) of the control signal may be monitored to quantify the amount of targets present in the sample after the iterative probing steps.

In some embodiments, a control probe may be employed to obtain quantitative information of the sample of interest, for example concentration of targets in the sample or molecular weight of the targets in the sample. For example, a control target (having known concentration or known molecular weight) may be loaded along with the sample of interest in a blotting technique. A control probe may be bonded to the control target and a control signal observed. The control signal may be then correlated with the signals observed from the sample of interest using methods described herein below.

In some embodiments, a control probe may be employed in the methods disclosed herein to provide for co-registration of multiple molecular information (obtained through the iterative probing steps) and the morphological information (obtained, e.g., using DAPI). In some embodiments, methods disclosed herein may include co-registration of multiple fluorescent images with the bright-field morphological images obtained e.g., using H&E. In some embodiments, the probes employed in the iterative probing steps may not have any common compartmental information that may be used to register with the H&E images. A control probe like a DAPI nuclear stain may be employed to co-register the nucleus stained with hematoxylin in the bright-field images with the fluorescent images. The fluorescent images and the bright-field images may be co-registered using image registration algorithms that may be grouped in two categories: intensity-based and feature-based techniques.

Correlating the First Signal and the Subsequent Signals

In some embodiments, a first signal, a subsequent signal, or the first signal and the subsequent signals may be analyzed to obtain information regarding the biological sample. For example, in some embodiments, a presence or absence of a first signal may indicate the presence or absence of the first target (capable of binding to the first binder) in the biological sample. Similarly, the presence or absence of a second signal may indicate the presence or absence of the second target (capable of binding to the second binder in the biological sample). In embodiments where multiple targets may be analyzed using a plurality of probes, the presence or absence of a particular signal may indicate the presence or absence of corresponding target in the biological sample.

In some embodiments, the observing steps may include a quantitative measurement of at least one target in the sample. In some embodiments, an intensity value of a signal (for example, fluorescence intensity) may be measured and may be correlated to the amount of target in the biological sample. A correlation between the amount of target and the signal intensity may be determined using calibration standards. In some embodiment, intensity values of the first and second signals may be measured and correlated to the respective target amounts. In some embodiments, by comparing the two signal intensities, the relative amounts of the first target and the second target (with respect to each other or with respect to a control) may be ascertained. Similarly, where multiple targets may be analyzed using multiple probes, relative amounts of different targets in the biological sample may be determined by measuring different signal intensities. In some embodiments, one or more control samples may be used as described hereinabove. By observing a presence or absence of a signal in the samples (biological sample of interest versus a control), information regarding the biological sample may be obtained. For example by comparing a diseased tissue sample versus a normal tissue sample, information regarding the targets present in the diseased tissue sample may be obtained. Similarly by comparing signal intensities between the samples (i.e., sample of interest and one or more control), information regarding the expression of targets in the sample may be obtained.

In some embodiments, the observing steps include co-localizing at least two targets in the sample. Methods for co-localizing targets in a sample are described in U.S. patent application Ser. No. 11/686,649, entitled "System and Methods for Analyzing Images of Tissue Samples", filed on Mar. 15, 2007; U.S. patent application Ser. No. 11/500,028, entitled "System and Method for Co-Registering Multi-Channel Images of a Tissue Micro Array", filed on Aug. 7, 2006; U.S. patent application Ser. No. 11/606,582, entitled "System and Methods for Scoring Images of a Tissue Micro Array, filed on Nov. 30, 2006, and U.S. application Ser. No. 11/680,063, entitled Automated Segmentation of Image Structures, filed on Feb. 28, 2007, now U.S. Pat. No. 8,036,462, issued on Oct. 11, 2011, each of which is herein incorporated by reference.

Figure 3:
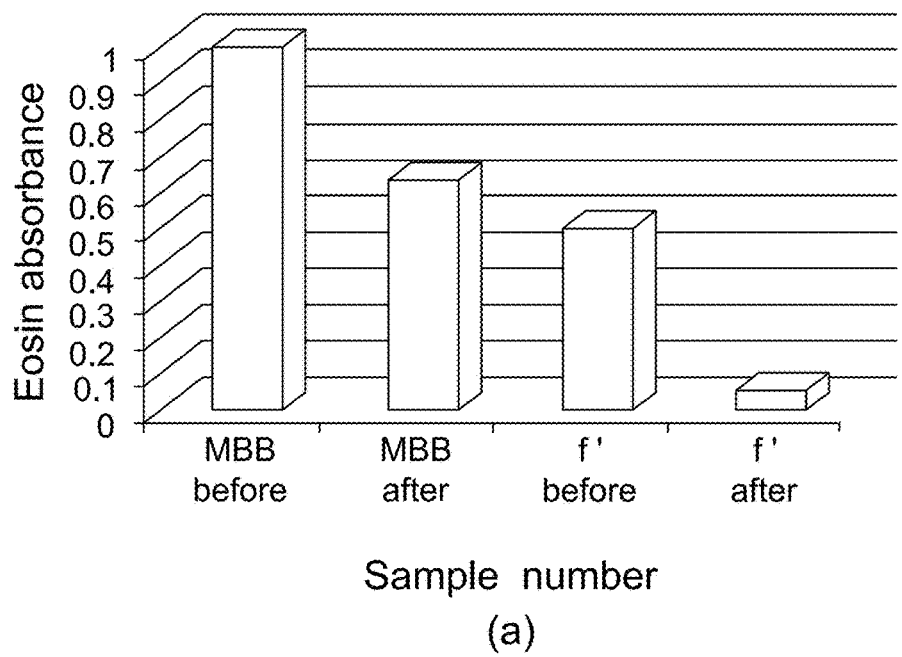
FIG. 3 are graphical representation comparing the performance of monobenzyltriphenyl borate (MBB) with f' (Formula I) for bleaching aqueous solutions of Eosin-Y (a) and Cy3 (b).
Figure 3:
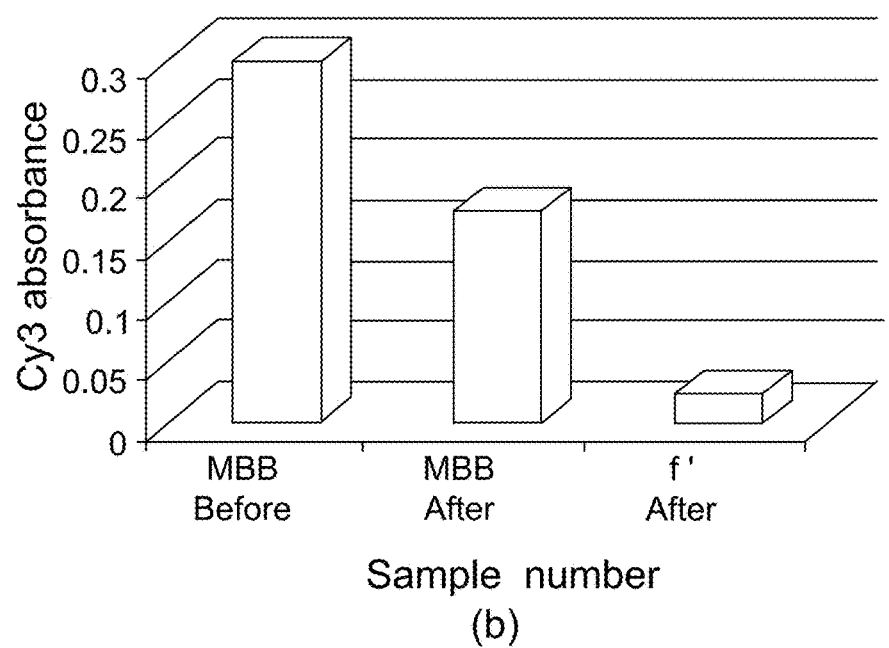

Other borate compound that were anionic-arylalkyl borates having a cationic counter ion have also been described in U.S. Pat. No. 8,568,991 issued Oct. 29, 2013 and U.S. patent application Ser. No. 13/786,747 filed Mar. 6, 2013 which are incorporated by reference. This class of borate compounds however was not as suited to xanthene base dyes, for example eosin and rhodamine that are routinely used for H&E staining and FISH. The borate compounds of Formula I show faster and more complete bleaching of eosin, in comparison to the borate salts having a cationic counter ion. For example FIG. 3 compares the performance of anionic borate, monobenzyltriphenyl borate (MBB) with f' (Formula I) for bleaching aqueous solutions of Eosin-Y (a) and Cy3 (b). In both instance bleaching was significantly improved with f.

Figure 4:
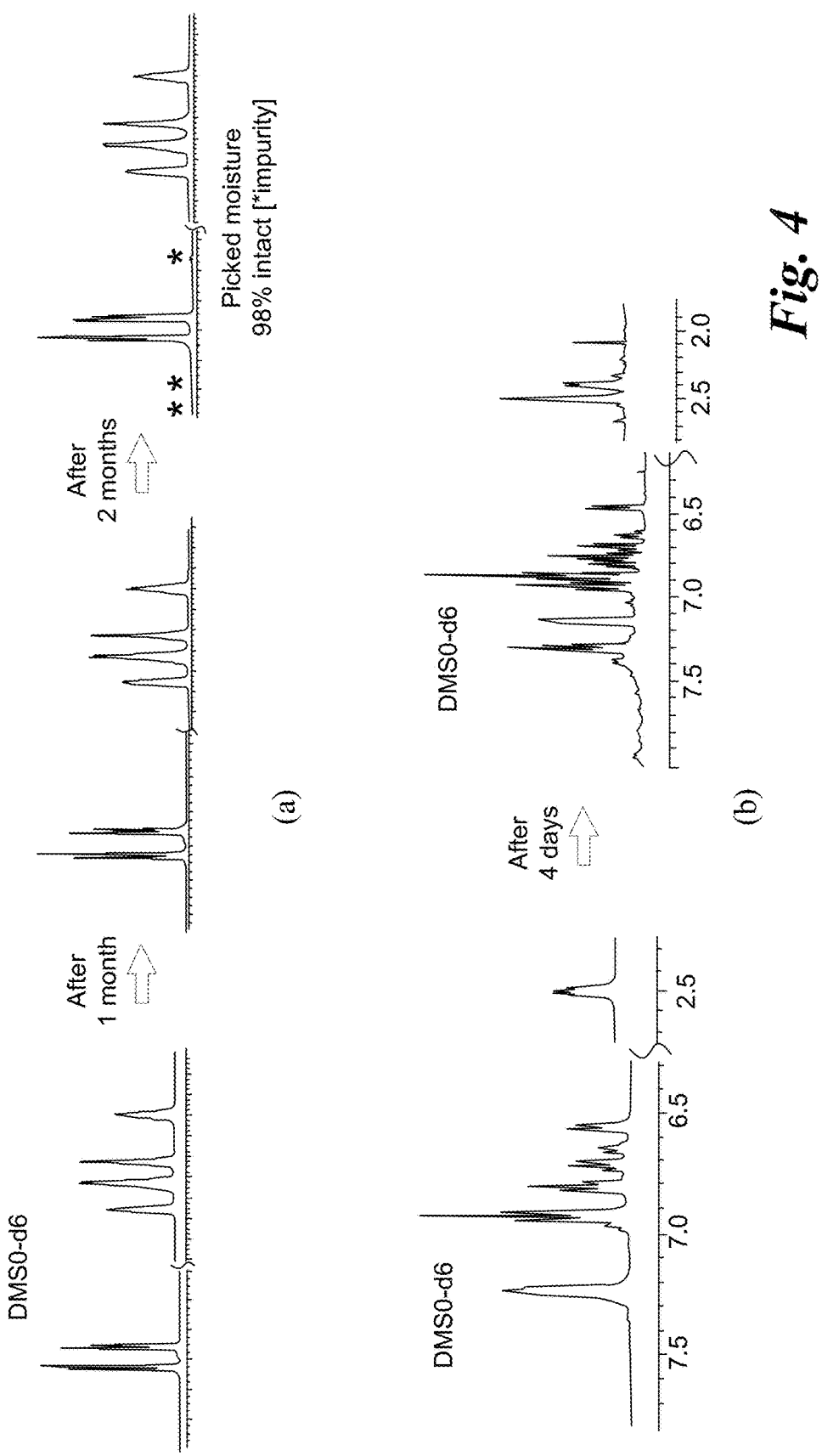
FIG. 4 are 1 HNMR scans showing degradation upon exposure to air (a) f' and (b) MBB.

The borate compounds of Formula I also show comparative improvement in shelf line. Exposure of the borate compound, in a solid form, to air for over 5 weeks shows no degradation by 1 HNMR. (FIG. 4 (a) f' and (b) MBB) In comparison the borate salts having a cationic counter ion shows evidence of decomposition within a relatively short period of time (<10 min) as evidence by MBB, which is a white solid stored inertly, becoming yellow in color immediately on exposure to air. In comparison f' (Formula I) shows exceptional stability showing very little decomposition (~2%) after 2 months of exposure to air.

In some embodiments, a location of the signal in the biological sample may be observed. In some embodiments, a localization of the signal in the biological signal may be observed using morphological stains. In some embodiments relative locations of two or more signals may be observed. A location of the signal may be correlated to a location of the target in the biological sample, providing information regarding localization of different targets in the biological sample. In some embodiments, an intensity value of the signal and a location of the signal may be correlated to obtain information regarding localization of different targets in the biological sample. For examples certain targets may be expressed more in the cytoplasm relative to the nucleus, or vice versa. In some embodiments, information regarding relative localization of targets may be obtained by comparing location and intensity values of two or more signals.

In embodiments employing blotting techniques, the observing steps may include observing a location of the signal on the blot. The location of the signal in the blot may be then correlated with calibration standards loaded along with the sample in the gel to obtain information regarding the molecular weight of the targets in the different bands. In some embodiments, a location of the signal on the blot may be correlated to a molecular weight of the target and the isoelectric point of the target, e.g., in 2D-PAGE. In some embodiments, structural proteins such as actin or tubulin may be probed using control probes in western blots to quantify the amount of targets in the sample.

In some embodiments, one or more of the observing or correlating step may be performed using computer-aided means. In embodiments where the signal(s) from the signal generator may be stored in the form of digital image(s), computer-aided analysis of the image(s) may be conducted. In some embodiments, images (e.g., signals from the probe(s) and morphological stains) may be overlaid using computer-aided superimposition to obtain complete information of the biological sample, for example topological and correlation information.

In some embodiments, one or more of the aforementioned may be automated and may be performed using automated systems. In some embodiments, all the steps may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

EXAMPLES

The following examples are intended only to illustrate methods and embodiments in accordance with the invention, and as such should not be construed as imposing limitations upon the claims.

Example 1

Synthesis of Borate Salts

A. Synthesis of Neutral Borate for a and b (Formula I):

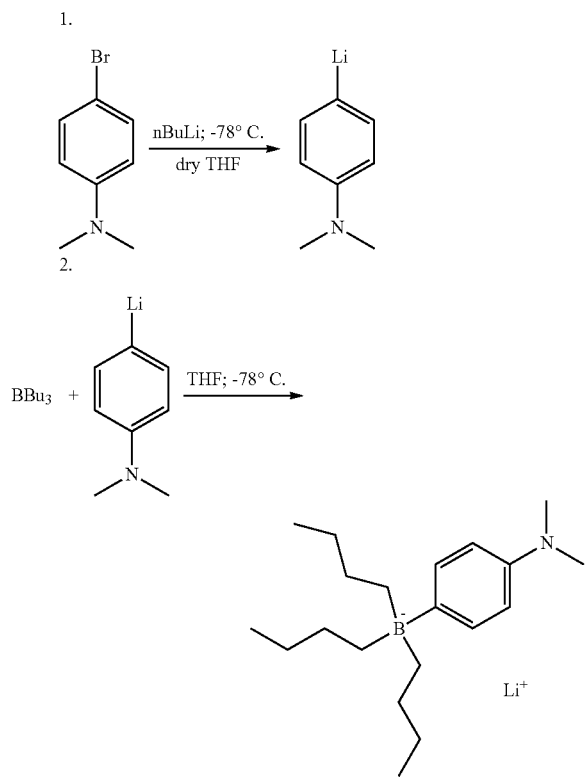

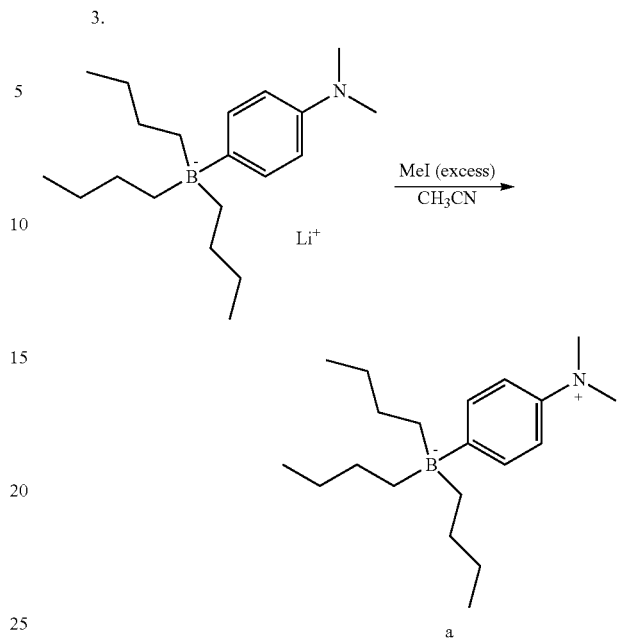

Step 1: In a 100 mL 3 neck round bottom flask, equipped with mechanical stirrer, was placed a solution of 6 g (0.03 mole) 4-bromo-N,N-dimethylaniline in 100 ml of dry THF under nitrogen atmosphere. The solution was cooled to −78° C. using a dry-ice acetone bath. To it was added, through syringe, 12 mL (0.03 mole) of a 2.5M solution of nBuLi in THF. White solid precipitated out of the solution as the reaction proceeded. The suspension was allowed to warm up to −40° C. slowly over 2-2.5 hrs after the addition was completed.

Step 2 After 2-2.5 hrs time period Step 1 flask was cooled back to −78° C. with acetone:dry-ice. To this solution, 30 mL of 1M BBu3.Me$_2$S was added dropwise through a syringe. As the contents got transferred, the white precipitate in Step-1 reaction redissolved to give a clear yellow solution. The reaction was allowed to warm to room temperature overnight.

The following day the reaction mixture was put on rotary evaporator to remove THF to obtain a yellow oily material and then replaced with 50 mL of acetonitrile. (Step-3) The reaction mixture in acetonitrile was transferred into a single neck 100 mL flask maintained under nitrogen blanket. To this solution Methyl Iodide 1.87 mL was added dropwise via a syringe and the reaction was allowed to stir for 8 hrs. The solvent was removed on rotary evaporator. H$_2$O (200 mL) was poured into the reaction mixture to allow the product to precipitate out. The white precipitate was suction filtered in a Buchner funnel and the precipitate was washed with more H$_2$O (100 mL) and followed by 100 mL of CH$_2$Cl$_2$ to remove any organic impurities. The off-white precipitate was dissolved into 50 mL of EtOH/Acetone 1:1 mixture and left in a nitrogen box for recrystallization to yield pure white powder product (6.7 g, 71.0% yield).

B. Synthesis of b Formula I:

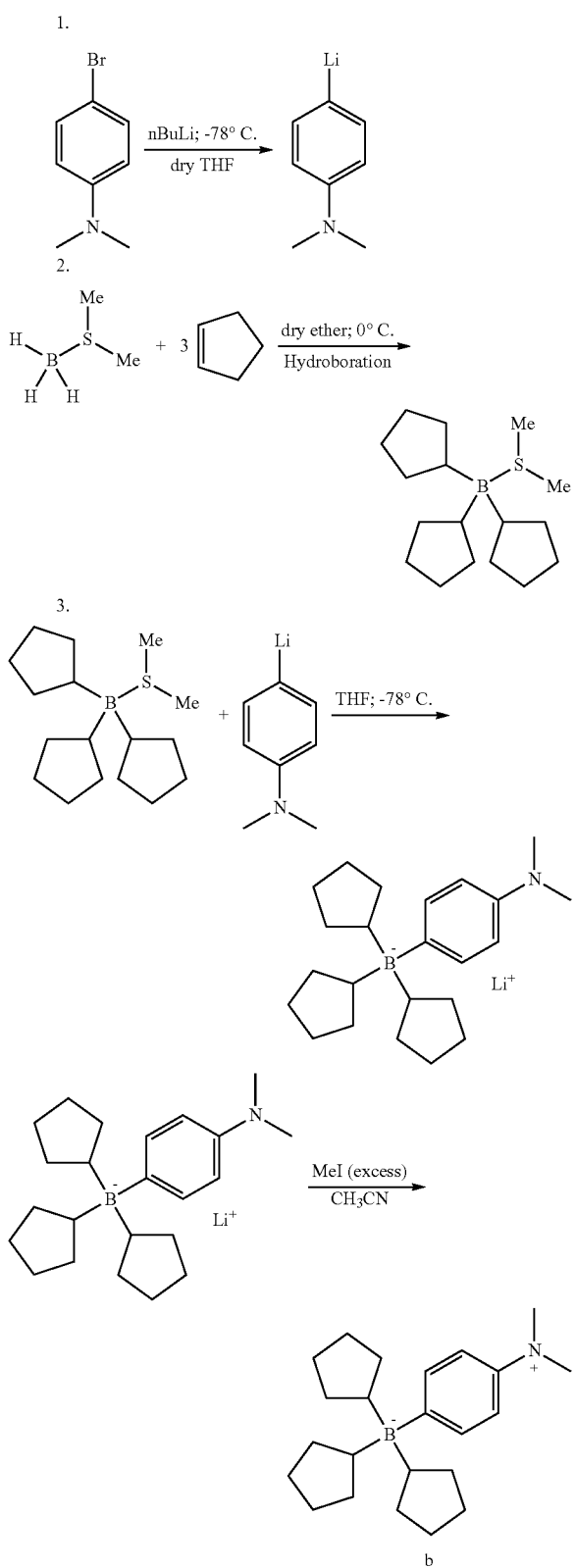

C Synthesis of Cationic Borate e' and f' (Formula I)

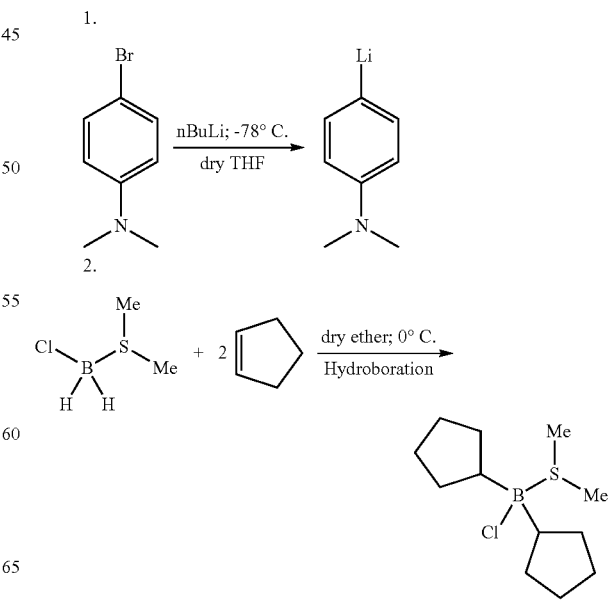

Step 1: In a 200 mL 3 neck round bottom flask, equipped with mechanical stirrer, was placed a solution of 5 g (0.025 mole) 4-bromo-N,N-dimethylaniline in 250 ml of dry THF under nitrogen atmosphere. The solution was cooled to −78° C. using a dry-ice acetone bath. To it was added, through syringe, 10 mL (0.025 mole) of a 2.5M solution of nBuLi in THF. White solid precipitated out of the solution as the reaction proceeded. The suspension was allowed to warm up to −40° C. slowly over 2-2.5 hrs after the addition was completed.

Step 2 was done in parallel with reaction-1 wherein, 6.6 mL cyclopentene (0.075 mol) was charged into a 100 mL three neck flask with 50 mL dry diethylether and stirred under nitrogen blanket and cooled to 0° C. To this stirring cold solution, 2.36 mL of $BH_3.Me_2S$ (0.025 mmol) adduct was added slowly (dropwise) over a period of 5 minutes. The reaction mixture was allowed to stir in ice-bath and warm up slowly to room temperature. After 2-2.5 hrs time period Step 1 flask was cooled back to −78° C. with acetone:dry-ice and Step 2 mixture was slowly cannulated into Step-1 contents under positive pressure of nitrogen. As the contents got transferred, the white precipitate in Step-1 reaction redissolved to give a clear solution. The reaction was allowed to warm to room temperature overnight.

The following day the reaction mixture was put on rotary evaporator to remove THF to obtain a oily material and then replaced with 50 mL of acetonitrile. (Step-4) The reaction mixture in acetonitrile was transferred into a single neck 250 mL flask maintained under nitrogen blanket and cooled to 0° C. To this solution Methyl Iodide 1.75 mL was added dropwise via a syringe and the reaction was allowed to stir for 8 hrs. The solvent was removed on rotary evaporator. $H_2O$ (200 mL) was poured into the reaction mixture to allow the product to precipitate out. The white precipitate was suction filtered in a Buchner funnel and the precipitate was washed with more $H_2O$ (100 mL) and followed by 100 mL of Hexane to remove any organic impurities. The off-white precipitate was dissolved into 50 mL of EtOH/Acetone 1:1 mixture and left in a nitrogen box for recrystallization to yield pure white powder product (5.5 g, 62.5% yield).

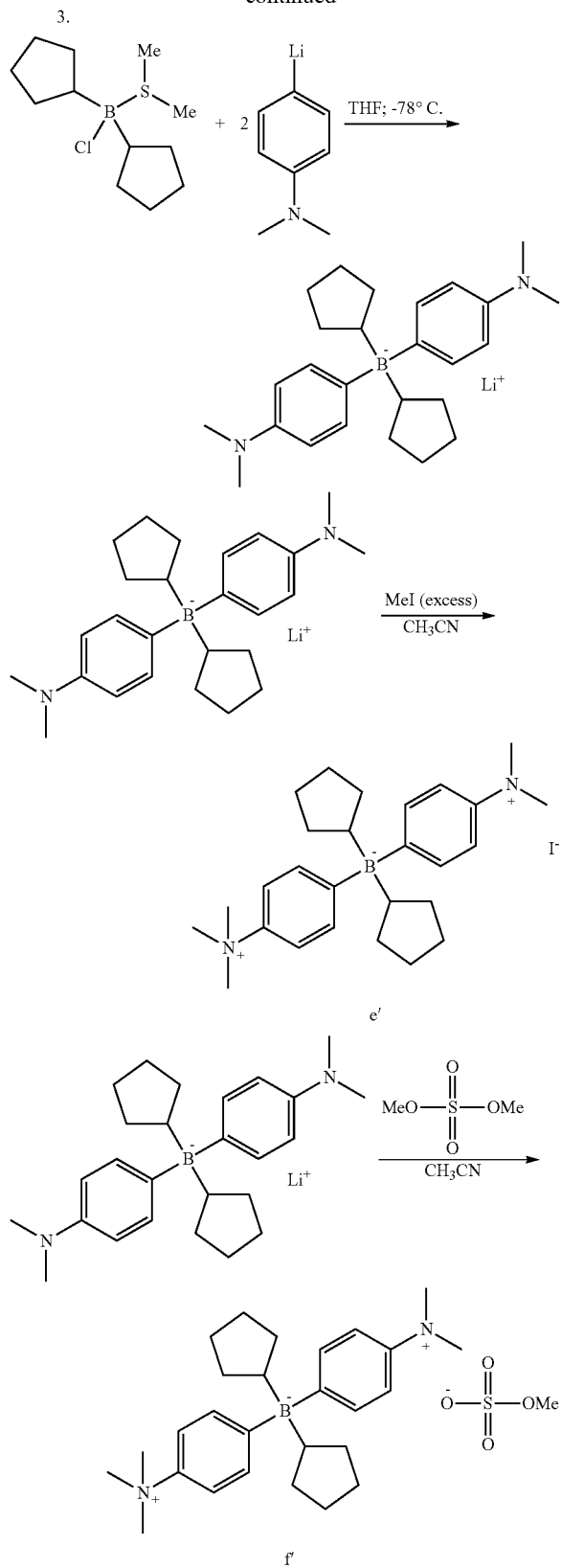

under nitrogen atmosphere. The solution was cooled to −78° C. using a dry-ice acetone bath. To it was added, through syringe, 20 mL (0.05 mole) of a 2.5M solution of nBuLi in THF. White solid precipitated out of the solution as the reaction proceeded. The suspension was allowed to warm up to −40° C. slowly over 2-2.5 hrs after the addition was completed.

Step 2 was done in parallel with reaction-1 wherein, 4.475 mL cyclopentene (0.05 mol) was charged into a 100 mL three neck flask with 50 mL dry diethylether and stirred under nitrogen blanket and cooled to 0° C. To this stirring cold solution, 2.64 mL of ChloroBorane.Me$_2$S (0.025 mmol) adduct was added slowly (dropwise) over a period of 5 minutes. The reaction mixture was allowed to stir in ice-bath and warm up slowly to room temperature. After 2-2.5 hrs time period Step 1 flask was cooled back to −78° C. with acetone:dry-ice and Step 2 mixture was cannulated into Step-1 contents under positive pressure of nitrogen. As the contents got transferred, the white precipitate in Step-1 reaction redissolved to give a clear solution (Step-3). The reaction was allowed to warm to room temperature overnight.

The following day the reaction mixture was put on rotary evaporator to remove THF to obtain an oily material and then replaced with 100 mL of acetonitrile. The reaction mixture in acetonitrile was transferred into a single neck 250 mL flask maintained under nitrogen blanket and cooled to 0° C. To this solution, either Methyl Iodide 6.22 mL (excess-4 eqs) was added dropwise via a syringe to synthesize e' (Formula I) or dimethyl sulfate 4.78 mL (0.04 mol) was added dropwise via a syringe to synthesize f' (Formula I). The reaction was allowed to stir for 8-12 hrs. The solvent was removed on rotary evaporator. H$_2$O (200 mL) was poured into the reaction mixture to allow the product to precipitate out. The white precipitate was suction filtered in a Buchner funnel and the precipitate was washed with more H$_2$O (100 mL). Later the white precipitate was washed with CH$_2$Cl$_2$ (200 mL) to remove any organic impurities. The white precipitate was dissolved into 50 mL of EtOH/Acetone 1:1 mixture and left in a nitrogen box for recrystallization to yield pure white powder product (e':7.0 g, 51% yield; f':7.2 g, 54% yield).

Example 2

Bleaching of Dyes in Solution

Figure 5:
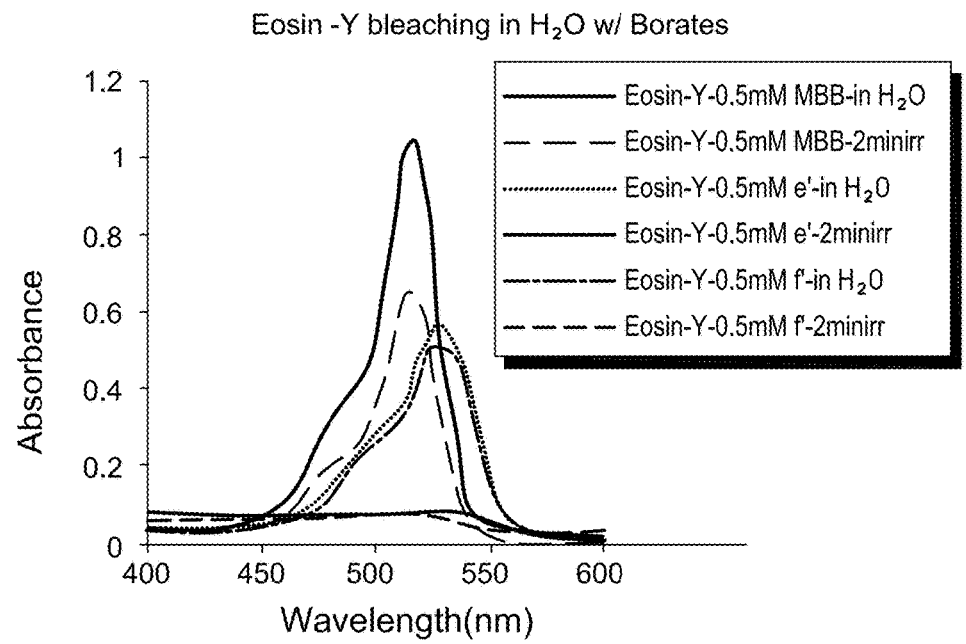
FIG. 5 shows a graph of UV-Vis analysis of Eosin-Y photobleaching studies in the presence of borates in water
Figure 6:
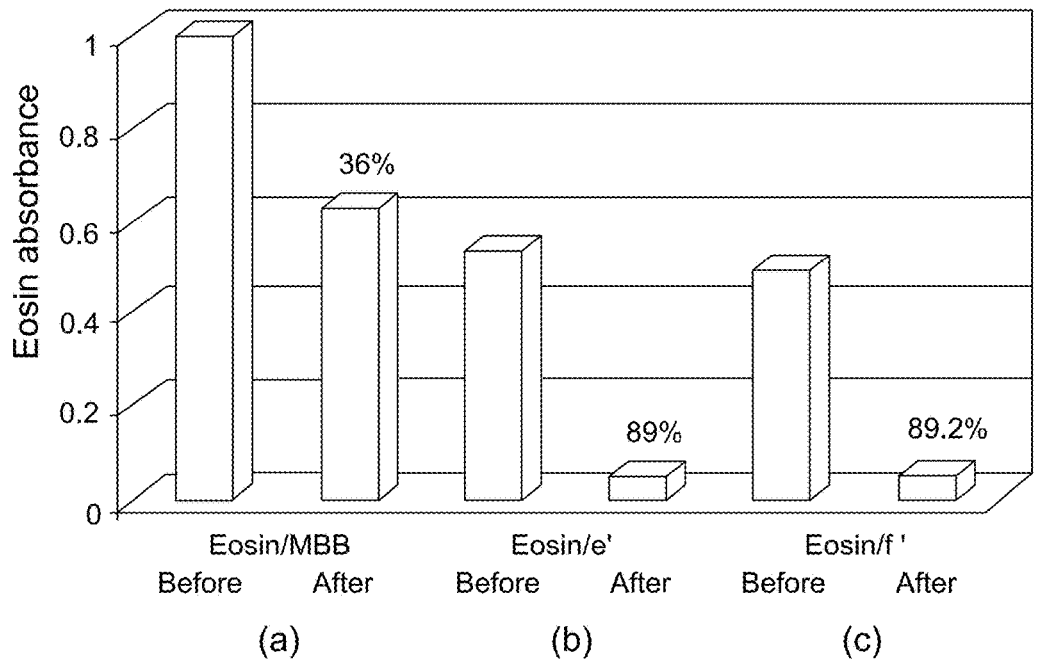
FIG. 6 is a bar graph comparing bleaching kinetics of eosin in water by different borates; MBB (a), e'(b), and f'(c) showing before and after irradiation; exposure to light.

A Eosin Y Bleaching with Borates in Water:

To a 2 mL solution of Eosin in water (2.26×10-5M solution), 2 mL of 0.5 mM of cationic Borate (e'), Cationic Borate (f') or anionic borate (MBB) were added, and the solution was irradiated for 1 minute using 100 W halogen lamp. The samples showed a visible difference after 1 min. FIG. 5 shows a graph of UV-Vis analysis of Eosin-Y photobleaching studies in the presence of borates in water. FIG. 6 is a bar graph comparing bleaching kinetics of eosin by different borates MBB (a), e' (b), and f' (c). The results demonstrate that the extent by which eosin photobleaching was improved with cationic borate salt when compared to anionic borate (MBB).

Figure 7:
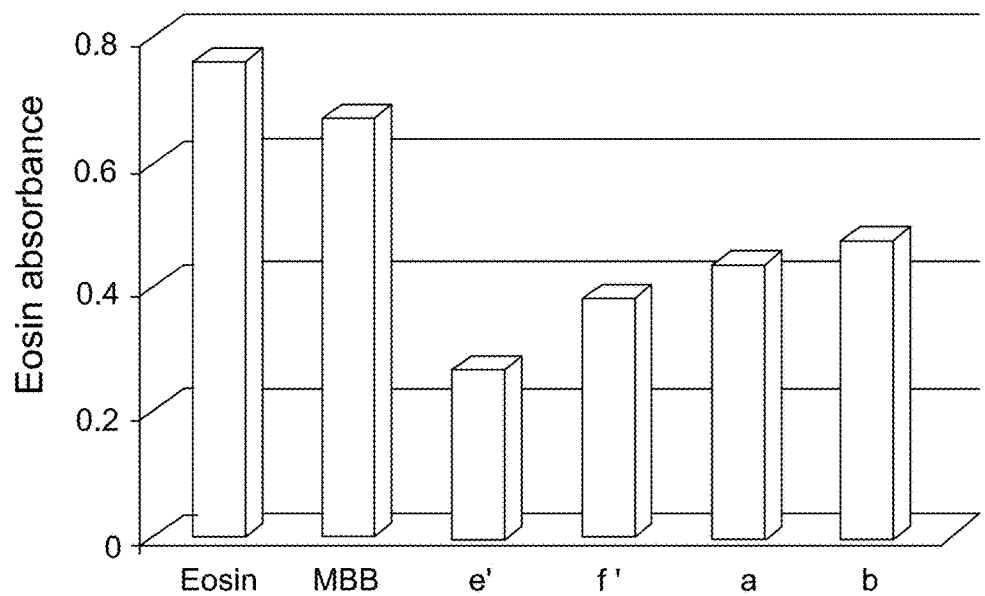
FIG. 7 is a bar graph shows bleaching of eosin in ethanol as measured by reduction in absorbance signal after 2 min irradiation with visible lamps; eosin signal with no borate added was used as the benchmark for comparing the bleaching kinetics in the presence of borates; anionic borate (MBB); cationic borate (e' and f') and neutral borate (a and b).

B Eosin Y Bleaching with Borates in Ethanol:

To a 2 mL solution of Eosin in ethanol (2.5×10-5M solution), 2 mL of 1 mM of anionic borate (MBB), a neutral borate a, (Formula I) or a neutral borate b (Formula I) were added and the solution was irradiated for 1-2 minutes using 100 W halogen lamp. Absorbance at λmax of dye was measured to monitor photobleaching, and the results were Step 1: In a 500 mL 3 neck round bottom flask, equipped with mechanical stirrer, was placed a solution of 10 g (0.05 mole) 4-bromo-N,N-dimethylaniline in 250 ml of dry THF plotted, as is shown in the bar graph plot of FIG. 7. The bar graph shows bleaching of eosin and reduction in signal after 2 min irradiation with visible lamps. Eosin signal with no borate added was used as the benchmark for comparing the bleaching kinetics in the presence of borates (anionic borate (MBB); cationic borate (e' and f') and neutral borate (a and b). The results demonstrate that the extent of Eosin photobleaching kinetics follows the order cationic>neutral>anionic borate salt. Results may be related to greater interactions of negatively charged eosin with cationic borate and or greater stability of cationic and neutral borates. The reactivity may also be influenced by the relative solubility of the borate and the solvents selected.

Figure 8:
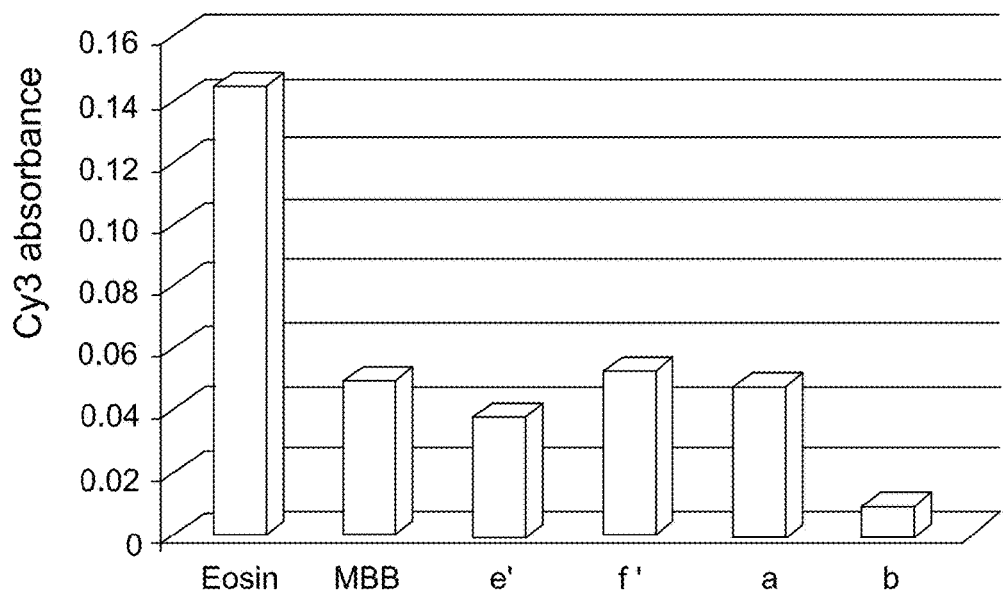
FIG. 8 is a bar graph compares the bleaching kinetics of Cy3 by different borates in ethanol; Cy3 with no borate added was used as the benchmark for comparing the bleaching kinetics in the presence of borates; anionic borate (MBB); cationic borate (e' and f') and neutral borate (a and b).

C. Cy3 Dye Bleaching with Borates in Ethanol:

To a 2 mL solution of previously hydrolyzed Cy3 bisreactive dye (GE Healthcare) in ethanol (2.5×10-5M solution), 2 mL of 1 mM solution of one of the following borates: anionic borate (MBB), neutral borate, a or b (Formula I), and cationic borates e' or f' in ethanol was added. Samples were irradiated for 1 minute using 100 W halogen lamp. The decrease in Cy3 absorbance at 552 nm was measured to monitor photobleaching, and the results were plotted, as is shown in FIG. 8. The bar graph compares the bleaching kinetics of Cy3 by different borates in ethanol. As shown the cationic and neutral borates performed well.

Figure 9:
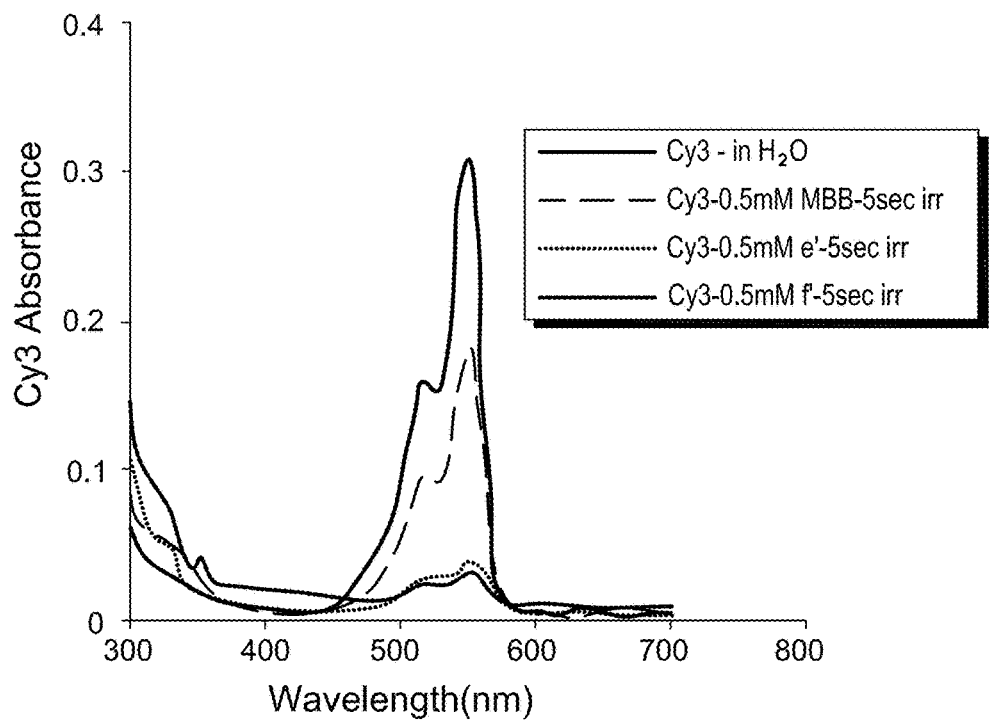
FIG. 9 is a graphical representation results of the CY3 bleaching with different borates; absorbance at 552 nm was measured to monitor photobleaching.
Figure 10:
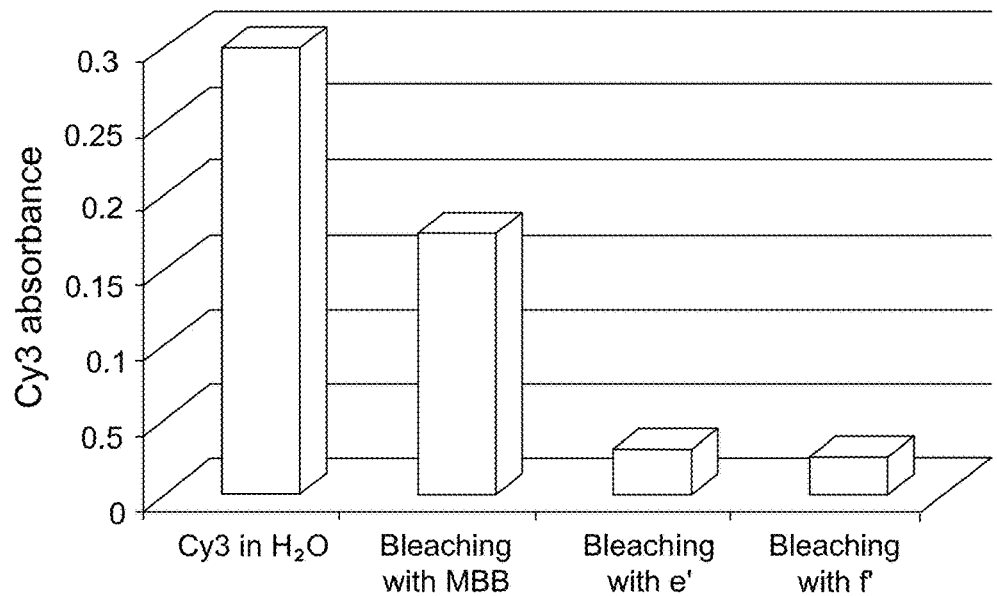
FIG. 10 is a bar graph comparing bleaching kinetics of Cy3 by different borates in an aqueous solution; cationic borate (e' and f') showed faster bleaching kinetics than anionic borate (MBB).

D. Cy3 Bleaching with Borates in Water:

To a 2 mL solution of previously hydrolyzed Cy3 bis reactive dye in water (3.4×10-5M solution), 2 mL of 0.5 mM solution of anionic borate (MBB), cationic borate (e') or cationic borate (f') were added and the solution was irradiated. FIG. 9 shows results of 5 sec irradiation using 100 W halogen lamp. The Cy3 absorbance at 552 nm was measured to monitor photobleaching and the results were plotted, as is shown in FIG. 9. FIG. 10 is a bar graph comparing bleaching kinetics of Cy3 by different borates. The cationic borate (e' and f) showed much faster bleaching kinetics than anionic borate (MBB).

E. Charge Transfer Complex Formation Between Eosin-Y and Cationic Borates:

A 50 ul of 1 mM eosin solution in water was further diluted to 3 ml with water and to this was added 1 mM solution of f' (Formula I) in water in 25 ul portions. UV-Vis spectrum was acquired after every 25 µL f' addition. As f' was added, a clear change in color to non-fluorescent pink was observed which intensified with every 25 µL f' addition.

The UV-Vis spectroscopic results showed a bathochromic (red-shift) of the Eosin-Y emission peak (518 nm shifts to 523 nm). This is believed to be due an electrostatic charge-transfer complex formulation between cationic borate: eosin-y complex.

Figure 11:
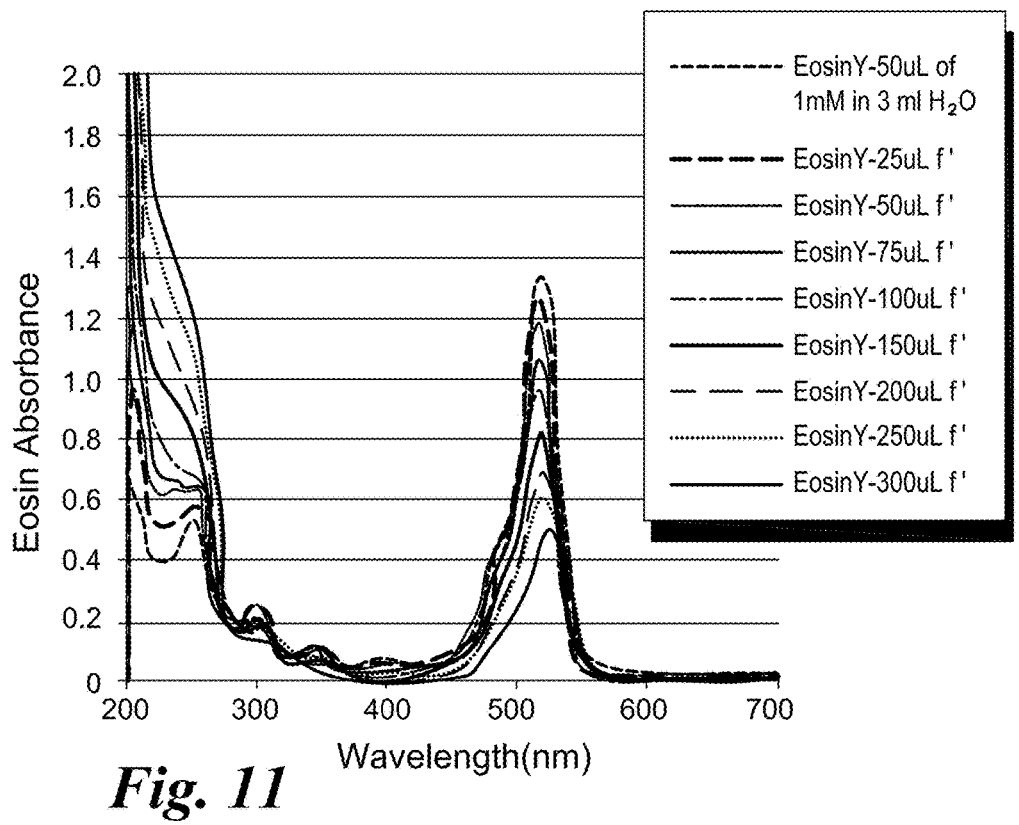
FIG. 11 shows UV studies on the f' titration in Eosin-Y solution without irradiation.
Figure 12:
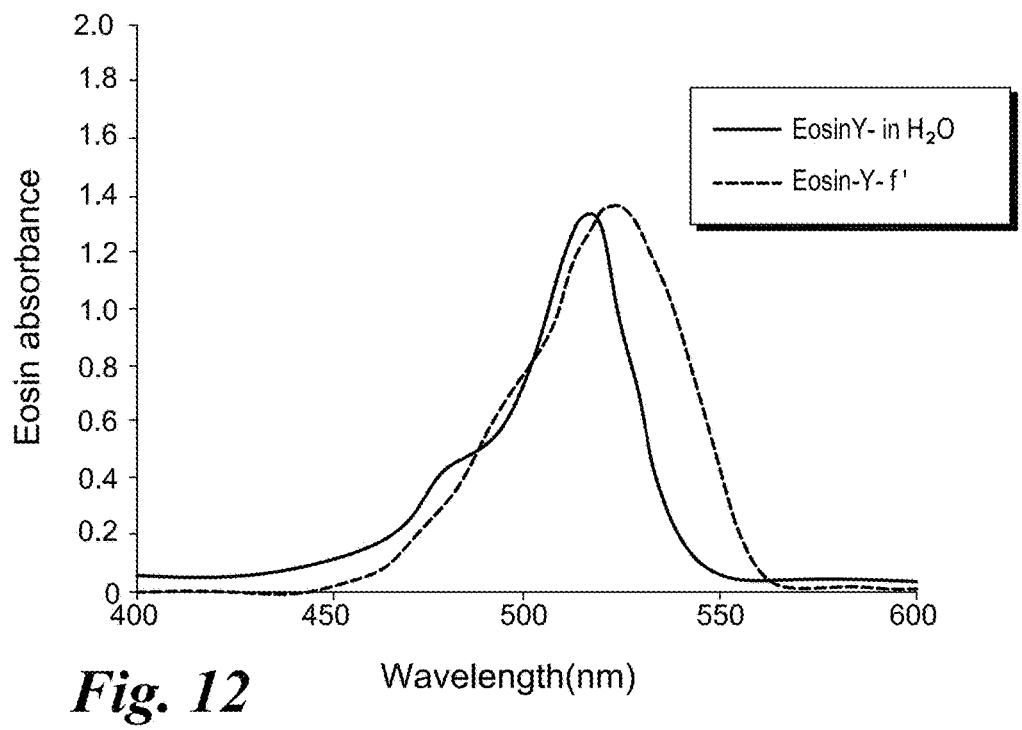
FIG. 12 shows the normalized UV-Vis spectrum before and after f' added without irradiation.

FIG. 11 shows UV studies on the f' titration in Eosin-Y solution. FIG. 12 shows the normalized UV-Vis spectrum before and after addition of 300 µl of f'. This phenomenon may be attributed to formation of charge-transfer complex between anionic Eosin-Y and cationic Borate. The electrostatic charge transfer formation is responsible for quenching of Eosin-Y fluorescence.

Example 3

Dye Bleaching in Tissue Sections

A. H&E Staining and Signal Removal

Human breast tissue array samples were obtained as tissue slides embedded in paraffin from Clarient (Huntsville, Ala.). Slides were baked at 60° C. for 15 minutes and then washed with xylene (1×10 min) to remove paraffin.

All the slides were stained with hematoxylin and eosin and coverslipped following the standard procedures in the literature (IHC World LLC, Protocol Database, Hematoxylin and Eosin (H&E) Staining Protocol). After staining, the images were obtained as described below.

Bright field and Fluorescence images were taken for all the slides using Leica bright field microscope and Olympus IX81 fluorescence microscope (Olympus Co., Tokyo, Japan respectively. For fluorescence imaging the following excitation filters were used: eosin 500/40 nm, Cy3 550/40 nm and Cy5 650/40 nm.

After imaging, samples were decoverslipped by incubation in xylenes overnight and hydrated by washing in four solutions of ethanol with concentrations decreasing in the order of 100%, 95%, 70%, and 50% followed by a wash with 1× phosphate buffer saline (PBS, pH 7.4). After rehydration, the slides were washed with 1×PBS. A ten minute incubation in 0.3% Triton X-100 in PBS was performed for membrane permeabilization of the tissue, followed by a wash with 1×PBS.

Figure 13:
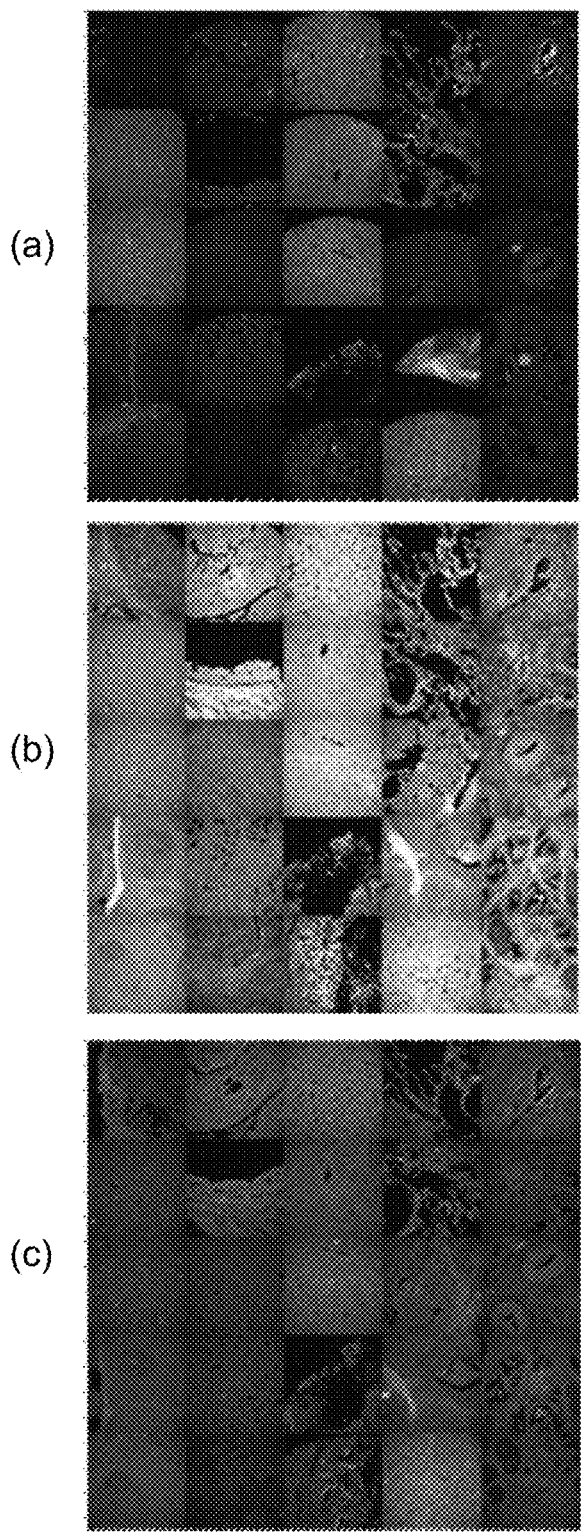
FIG. 13 are images of H&E stained and bleached slides further subjected to several rounds of protein multiplexing. Images show effective bleaching of residual eosin in various tissues on a tissue microarray using PICB with f'; a) a montage of images of different tissue types from a control (non H&E stained or bleached slide) slide showing tissue autofluorescence, b) residual eosin fluorescence in different tissue after H&E staining and subsequent hydration and antigen retrieval, and c) residual signal after slide in b was subjected to further bleaching by PICB using f'.

Hydrated slides were treated with dual-buffer heat-induced epitope retrieval. Slides were immersed in a preheated 70° C. Citrate Buffer pH 6.0 (Vector Unmasking Solution), further heated in a pressure cooker to a temperature of 110° C., held at this temperature for 4 minutes, and then gradually cooled (final temperature of 96° C.). Slides were in Citrate Buffer for a total of twenty minutes and then transferred to hot (96° C.) Tris-EDTA Buffer pH 9.0 and allowed to stand in the cooker at atmospheric pressure with gradual cooling for twenty minutes. This was followed by cooling down at room temperature for ten minutes and a series of washes in 1×PBS. Slides were imaged by brightfield and fluorescence microscopy. While brightfield images showed practically complete removal of hematoxylin and eosin colors, bright fluorescence was observed from residual eosin as shown in FIG. 13 (b). As shown, for comparison, a slide with serial section from the same TMA block without H&E staining was processed through slide clearing (deparaffinization and hydration) and antigen retrieval. The control slide, FIG. 13a, was imaged to capture tissue autofluorescence. Images in FIG. 13b are substantially brighter than 13a.

Following antigen retrieval the slides were blocked against nonspecific binding by incubating overnight in a 10% donkey serum, 3% bovine serum albumin (BSA) solution at 4° C.

Residual Eosin Bleaching was accomplished as follows: All H & E slides after blocking were incubated in 500 uL of 0.15 mM f' solution in dark for 11 min, followed by a quick wash in 1×PBS. 125 uM DABCO in IX PBS was added to these slides and slides were irradiated for 13.5 min. Following irradiation slides were again dipped in PBS for a minute and the above cycle of f' incubation, wash followed by irradiation in the presence of DABCO was repeated two more times. Slides are washed with 50% ethanol for 1 min×3 and PBS 5 min×3, and, coverslipped with 90% glycerol, 4% propyl gallate and 1% Dabco mounting media. Slides were imaged as shown in FIG. 13. FIG. 13 shows autofluorescence of tissue in a control slide (a) imaging after H&E staining and antigen retrieval (13b) and after signal removal by PICB using f (13c). Residual eosin signal was mostly removed and the images after bleaching step are substantially diminished in intensity compared to images of the same slide after H&E staining, hydration and antigen retrieval and are comparable to the control images.

B. i) Immunofluorescence Staining and Imaging after H&E Staining and Signal Removal Following the above procedures for H&E staining and signal removal with f, slides were stained with DAPI and cover slipped. Alternatively previously H&E stained and imaged slides that had been archived were processed through decoverslipping, hydration, antigen retrieval, blocking and PICB bleaching steps prior to staining with DAPI and coverslipping. Images were taken at 20× prior to protein staining to record the autofluorescence of any unbleached eosin and tissue in Cy2, Cy3 and Cy5 channels. Slides were decoverslipped in 1×PBS and stained with Cy3 conjugated PCK26/AE1 antibody cocktail as a pan cytokeratin marker that stains multiple keratins in the tissue. Staining quality was similar to the staining of a control slide that had not been subjected to H&E staining and subsequent bleaching of residual eosin signal.

B. ii) Immunofluorescence Imaging and Bleaching of Immunofluorescence Signal

Figure 14:
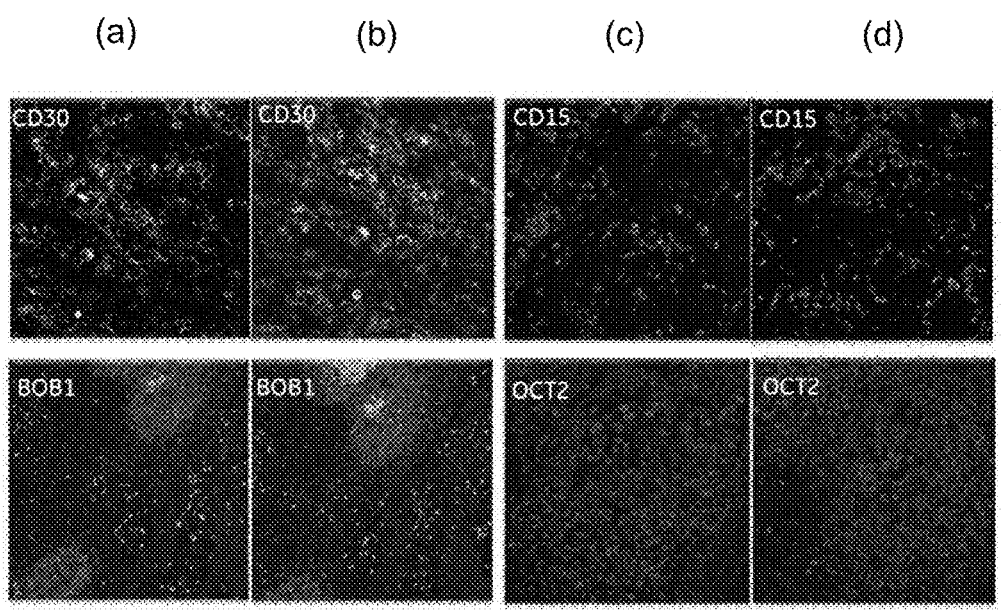
FIG. 14 are images of staining of various protein targets on HL tissue. Slides were subjected to staining of two protein targets, imaged and bleached with f' and then stained for two additional protein targets. Images show staining is comparable to the staining observed in control; (a) and (c) are f' bleached slides compared to their respective controls (b) and (d) (between protein staining rounds, control slides were bleached with basic peroxide process described in Gerdes et. al., PNAS 2013, v 110, 11982-7).

The above procedures for H&E staining and signal removal was performed as in Example 3A above and slides stained with Cy3 conjugated anti-CD30 and Cy5 conjugated anti-Bob1 as described in example 3B. Slides were imaged and then bleached by incubating the slides in a solution of f' (0.15 mM in PBS containing 125 uM DABCO) and simultaneously irradiating with white light. After dye bleaching slides were stained with another set of antibodies using the same fluorophores, Cy3-conjugated anti-CD15 and Cy5 conjugated anti-Oct2. For comparison control slides that hadn't been stained with H&E but were processed through antigen retrieval and blocking steps were also stained with Cy3 conjugated anti-CD30 and Cy5 conjugated anti-Bob1 antibody cocktail. After imaging, these slides were bleached with basic peroxide (U.S. Pat. No. 7,629,125) prior to staining with anti-CD15 and anti-Oct2 antibodies. As shown in FIG. 14 staining of various protein targets is comparable to the staining observed in control slides indicating that bleaching of residual eosin or bleaching of cyanine dyes in subsequent steps with f' doesn't affect antigens; a, (staining after H&E bleaching) and c, (staining after Cy3 dye bleaching) are f' bleached slides compared to their respective controls (b) and (d). Control slides were bleached with basic peroxide process described in Gerdes et. al., PNAS 2013, v 110, 11982-7.

B. iii) Additional Rounds of Staining

Figure 15:
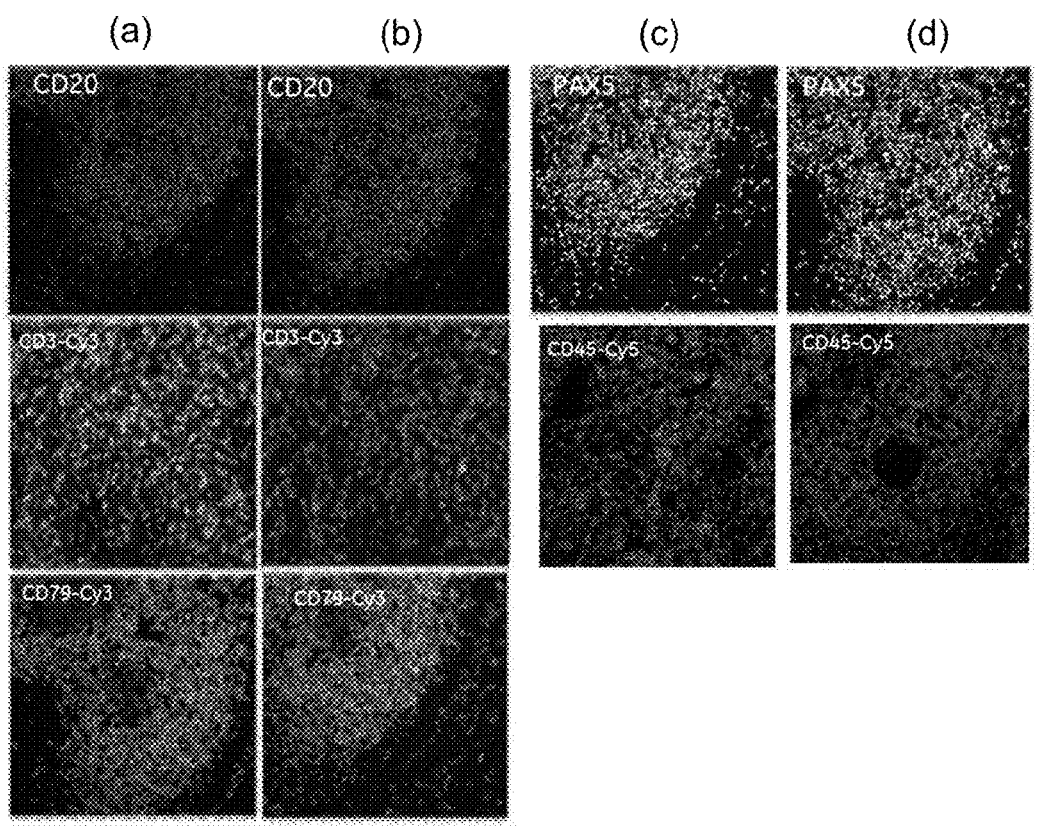
FIG. 15 are images of three additional rounds of protein staining similar to those shown in FIG. 14 showing cycling with f' were again comparable to those observed with control slides; (a) and (c) are f' bleached slides while (b) and (d) are the respective controls.

Slides from the above procedure (Bii) were subjected to additional rounds of protein staining, imaging and signal removal. Controls slides were similarly processed as described in the above procedure. Results (FIG. 15) from cycling with f' were again comparable to those observed with control slides; (a) and (c) are f' bleached slides while (b) and (d) are the respective controls.

C. H & E and Fluorescence In Situ Hybridization (FISH) on the Same Slide

Slides were H&E stained and bleached as described above. Alternatively previously imaged and archived H&E slides were processed through the steps of decoverslipping, hydration, antigen retrieval, blocking and bleaching with f' as described above for freshly stained H&E slides.

Figure 16:
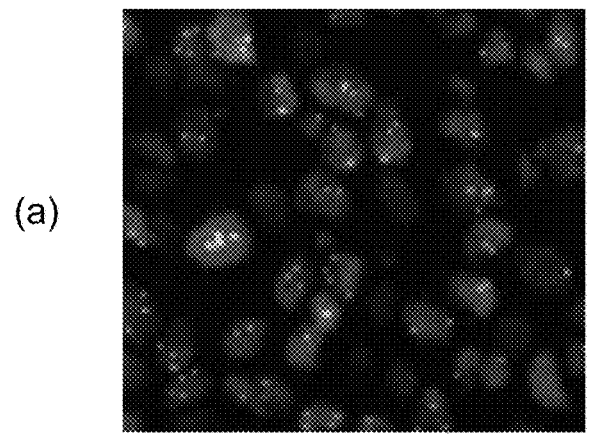
FIG. 16 are images of FISH on previously H&E stained (freshly stained or archived) and PICB bleached slides and their comparison to FISH signal on a control slide (a) control slide without H&E subjected to FISH (b) archived H&E slide bleached by PICB using f and subjected to FISH (c) freshly stained H&E slide bleached by PICB using f' and subjected to FISH.
Figure 16:
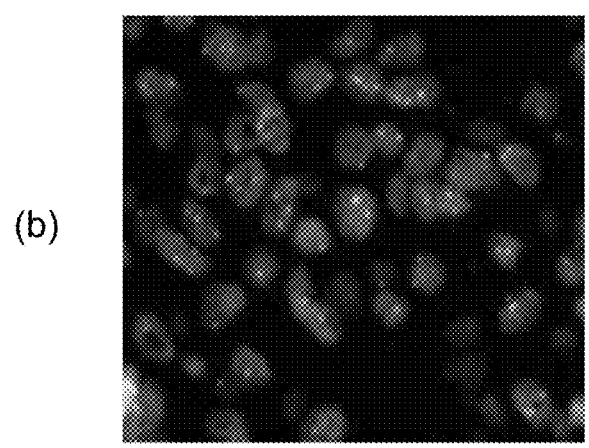
Figure 16:
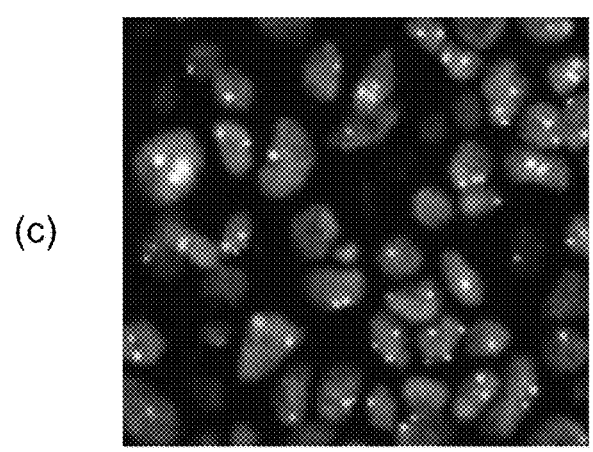

Slides were immersed in a pre-warmed 0.1% pepsin solution for 8 minutes then placed in room temperature PBS for 2 minutes. Samples were re-fixed in 4% formalin for 10 minutes then washed 2×5 minutes in PBS. Slides were dehydrated in ethanol series 50%, 70%, and 95%, 2 minutes each and allowed to dry on bench top for 10 minutes. Pre-mixed dual Her2/CEP17 probe was vortexed, spun, and added to samples. Samples were coverslipped and sealed with a rubber sealant per usual practice. After allowing rubber cement to cure for 10 minutes, probes were hybridized in Thermobrite cycler: 80° C. denaturation for 10 minutes followed by 37° C. incubation overnight. Rubber cement was removed and slides were decoverslipped in preheated 37° C. 2×SSC for 5 minutes. Slides were then transferred into a preheated (72° C.) solution of 2×SSC containing 0.3% NP-40 and incubated for 2 minutes. Slides were washed 2×2 minutes with 2×SSC, removed from buffer to dry, coverslipped with 4% DABCO in 90% glycerol/2× SSC, and imaged on an Olympus IX81 fluorescence microscope using a 40× objective with following exposure times: for DAPI (2 ms), spectrum green (CEP17-200 ms), and spectrum orange (Her2-400 ms). A z-stack value of 12, gain of 10, and step size of 0.75µ were used. Micrograph Images are shown in FIG. 16 showing equivalent FISH signal to a control slide (16a) that was not subjected to H&E staining and PICB. Both freshly H&E stained (16c) and previously H&E stained and archived slides (16b) showed similar staining.

D. Multiplex DNA FISH Analysis by Iterative FISH Staining and Signal Removal Using f' (Formula I).

Step 1: Bleaching:

The bleaching solution for DNA FISH multiplexing contains 0.15 mM f' and 125 µm Dabco in water; the following process was used. After FISH imaging is done as in example 3C, slides were decoverslipped by shaking in PBS. Slides were placed in a slide holder and tissue was covered with 300-500 µl of f'/DABCO solution. Slide tray was placed in the center of the rayonet reactor, door was closed, and samples were irradiated for 20 minutes by turning on the lamps. The slide tray was removed from the reactor, solution was drained off the slides and slides were washed as follows; 3×1 minute 50% EtOH followed by 3×5 minute PBS.

Figure 17:
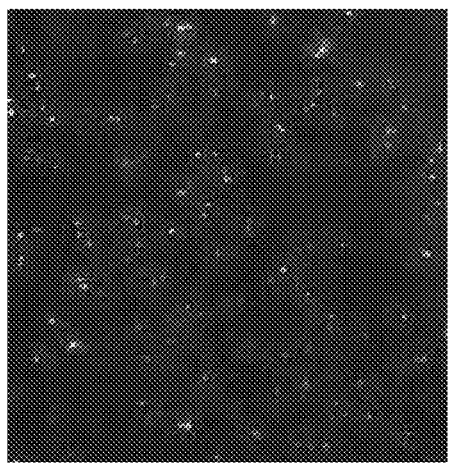
FIG. 17 are micrograph images of DNA FISH analysis showing the HER2 FISH signal on a previously unstained slide (a) compared to slide previously subjected to 4 rounds of FISH staining of other genes (and bleaching by PICB using f) before staining for HER2 (b).
Figure 17:
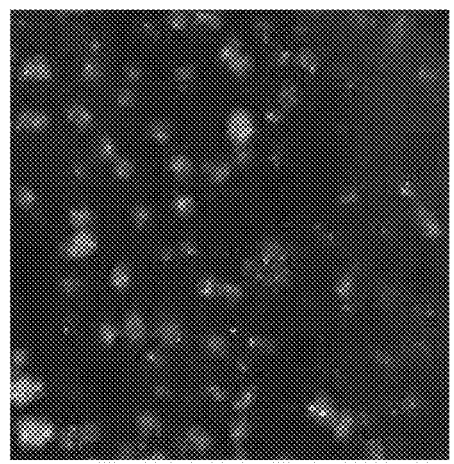

Step 2: Hybridization of New Probe:

After drying excess liquid surrounding the tissue, 10 ul of diluted Vysis hyb buffer (ie. 7 ul of buffer/3 ul of water) was added to the tissue and coverslipped with 10×10 glass coverslip. Slides were incubated on Thermobrite at 80° C. for 10 minutes (Mock denaturation) then removed from Thermobrite and decoverslipped as in Example 3. They were stained with DAPI for 2 minutes, washed in 1×PBS for 5 minutes, re-coverslipped then background imaged at same exposure times used for the previous probe imaging. Following imaging, slides were decoverslipped, dehydrated with EtOH series, and a new probe was hybridized as described above in example 3C. After hybridization, excess probe was removed as described above and slides were imaged to capture signal from the newly hybridized probes. This process of bleaching and hybridization of new probes was repeated three more times to enable five round DNA FISH. Results were compared with slides stained for individual probes separately as controls and were found to be of equivalent quality. FIG. 17 are micrograph images of DNA FISH analysis showing the control with no additional rounds of staining (a) compared to five rounds of staining (b).

What is claimed is:

1. A method of probing multiple targets in a biological sample comprising:
   (a) providing a biological sample containing multiple targets;
   (b) binding at least one probe to one or more targets present in the sample;
   (c) observing a signal from the at least one probe bound in step (b);

(d) contacting the sample comprising the bound probe of step (b) with a borate compound of Formula I;

$$R_1R_2R_3R_4B(X)_n \qquad I$$

where each of $R_1$, $R_2$, $R_3$ and $R_4$ is, independently, an alkyl, an alkylaryl, an arylalkyl, or an aryl, with the proviso that at least one of $R_1$, $R_2$, $R_3$ and $R_4$ is an alkyl group and at least one of $R_1$, $R_2$, $R_3$ and $R_4$ is positively charged X is an anion; and n equals 0, 1, 2, or 3;

(e) irradiating the sample of step (d); and (f) analyzing the sample for one or more targets.

2. The method of claim 1, wherein the probe in step (b) comprises an optical signal generator, and the signal observed in step (c) is an optical signal.

3. The method of claim 2, wherein the probe in step (b) comprises a fluorescent signal generator, and the signal observed in step (c) is a fluorescent signal.

4. The method of claim 3, wherein the fluorescent signal generator is a xanthene dye.

5. The method of claim 4, wherein the xanthene dye is eosin or fluorescein.

6. The method of claim 3, wherein the fluorescent signal generator comprises a cyanine dye.

7. The method of claim 6, wherein the cyanine dye is Cy3 or Cy5.

8. The method of claim 2, wherein irradiation of sample in step (e) initiates a photoreaction that substantially inactivates the optical signal generator by photoactivated chemical bleaching.

9. The method of claim 1, wherein irradiating the sample in step (e) is carried out in the presence of a buffer at pH of 5-9.

10. The method of claim 1, wherein steps (d) and (e) are carried out at the temperature of 4-50° C.

11. The method of claim 1, wherein irradiating the sample in step (e) is accomplished by exposing the sample to light of 350 nm-1.3 μm in wavelength.

12. The method of claim 11, wherein irradiating the sample in step (e) is accomplished by exposing the sample to light of 500-700 nm in wavelength.

13. The method of claim 1, wherein the steps (d) and (e) are performed for about 20 seconds to about 15 minutes.

14. The method of claim 1, wherein prior to step (e), the sample is rinsed with a buffer to remove excess borate.

15. The method of claim 1, wherein analyzing the sample comprises:
binding at least one probe to one or more targets present in the sample of step (e); and
(ii) observing a signal from the probe bound in step (i).

16. The method of claim 15, wherein steps (d)-(ii) are repeated one or more times.

17. The method of claim 15, further comprising measuring one or more intensity values of the signal observed in observing step (c), step (ii), or steps (c) and (ii).

18. The method of claim 17, further comprising correlating the intensity value with an amount of target present in the sample.

19. The method of claim 15, wherein the probe in step (b) and the probe in step (i) each comprise a signal generator, wherein the signal generator in step (b) is different from the signal generator in step (i).

20. The method of claim 1, wherein at least one of $R_1$, $R_2$, $R_3$ and $R_4$ is a 4-(trimethylamino)phenyl group.

21. The method of claim 1, wherein at least one of $R_1$, $R_2$, $R_3$ and $R_4$ is a 3-(trimethylamino)propyl group.

22. The method of claim 1, wherein at least two of $R_1$, $R_2$, $R_3$ and $R_4$ are positively charged.

23. The method of claim 1, wherein Formula I is

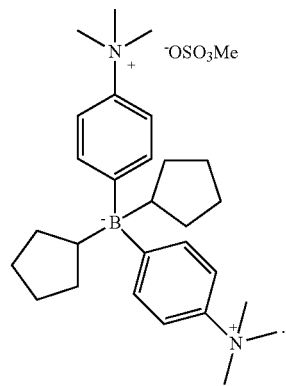

24. The method of claim 1, wherein more than one probe is bound to two or more targets.

25. The method of claim 1, where n equals 1, 2, or 3.

26. The method of claim 25, wherein X is selected from the group consisting of a halide, sulfonate, acetate, nitrate, phosphate ester and a carboxylate.

27. The method of claim 1, wherein more than one probe is bound to one target.

28. The method of claim 1, wherein the multiple targets are selected from the group consisting of peptides, proteins, nucleic acids, polysaccharides, lipids, enzymes, enzyme substrates, ligands, receptors, antigens, haptens and combinations thereof.

29. The method of claim 1, wherein the biological sample is a tissue sample.

* * * * *